United States Patent
Chen et al.

(10) Patent No.: US 10,661,090 B2
(45) Date of Patent: May 26, 2020

(54) IMPLANTABLE MEDICAL DEVICE BATTERIES WITH MILLED FLUORINATED CARBON FIBERS, DEVICES, AND METHODS

(71) Applicant: Medtronic, Inc., Minneapolis, MN (US)

(72) Inventors: Kaimin Chen, Shoreview, MN (US); Gaurav Jain, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 565 days.

(21) Appl. No.: 15/386,160

(22) Filed: Dec. 21, 2016

(65) Prior Publication Data

US 2018/0169421 A1 Jun. 21, 2018

(51) Int. Cl.
| | | |
|---|---|---|
| A61B 5/02 | (2006.01) | |
| A61N 1/378 | (2006.01) | |
| H01M 6/02 | (2006.01) | |
| H01M 4/04 | (2006.01) | |
| H01M 4/583 | (2010.01) | |
| H01M 4/38 | (2006.01) | |

(Continued)

(52) U.S. Cl.
CPC ........... *A61N 1/3787* (2013.01); *A61B 5/046* (2013.01); *A61B 5/0456* (2013.01); *A61N 1/36514* (2013.01); *A61N 1/36535* (2013.01); *A61N 1/36564* (2013.01); *A61N 1/378* (2013.01); *A61N 1/37235* (2013.01); *A61N 1/3956* (2013.01); *A61N 1/3962* (2013.01); *A61N 1/3975* (2013.01); *H01M 4/04* (2013.01); *H01M 4/1393* (2013.01); *H01M 4/382* (2013.01); *H01M 4/5835* (2013.01); *H01M 4/625* (2013.01); *H01M 6/02* (2013.01); *A61B 2560/0219* (2013.01); *H01M 2220/00* (2013.01)

(58) Field of Classification Search
None
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |

(Continued)

FOREIGN PATENT DOCUMENTS

| | | |
|---|---|---|
| EP | 1816692 B1 | 8/2007 |
| WO | 2007/091995 A3 | 8/2007 |
| WO | 2011068825 A1 | 6/2011 |

OTHER PUBLICATIONS (PCT/US2017/067008) PCT Notification of Transmittal of the International Search Report and the Written Opinion of the International Searching Authority, dated Mar. 27, 2018, 14 pages.

*Primary Examiner* — Eric J Messersmith
(74) *Attorney, Agent, or Firm* — Mueting, Raasch & Gebhardt, P.A.

(57) ABSTRACT

An implantable medical device comprising a battery cell including: an anode; a cathode including fluorinated carbon particles; a separator between the anode and the cathode; and an electrolyte contacting the anode, the cathode, and the separator; wherein greater than 50 vol-% of the fluorinated carbon particles have a particle size within a range of 2 microns to 10 microns, and greater than 50% by number have an aspect ratio within a range of 1:1.2 to 1:8.

10 Claims, 17 Drawing Sheets

(51) Int. Cl.
  *A61N 1/39* (2006.01)
  *A61B 5/046* (2006.01)
  *A61N 1/365* (2006.01)
  *A61N 1/372* (2006.01)
  *A61B 5/0456* (2006.01)
  *H01M 4/1393* (2010.01)
  *H01M 4/62* (2006.01)

(56) References Cited

U.S. PATENT DOCUMENTS

| | | |
|---|---|---|
| 5,221,453 A | 6/1993 | Crespi |
| 5,344,431 A | 9/1994 | Merritt et al. |
| 5,439,760 A | 8/1995 | Howard et al. |
| 5,474,858 A | 12/1995 | Merritt |
| 5,545,186 A | 8/1996 | Olson et al. |
| 5,716,729 A | 2/1998 | Sunderland et al. |
| 5,755,736 A | 5/1998 | Gillberg et al. |
| 5,958,623 A | 9/1999 | Kozawa et al. |
| 6,017,656 A | 1/2000 | Crespi et al. |
| 6,066,413 A | 5/2000 | Aymard et al. |
| 6,130,005 A | 10/2000 | Crespi et al. |
| 6,783,888 B2 | 8/2004 | Gan et al. |
| 7,824,805 B2 | 11/2010 | Howard et al. |
| 8,105,714 B2 | 1/2012 | Schmidt et al. |
| 9,065,145 B2 | 6/2015 | Schmidt et al. |
| 9,077,030 B2 | 7/2015 | Norton et al. |
| 9,130,229 B2 | 9/2015 | Chen et al. |
| 9,186,680 B2 | 11/2015 | Kume et al. |
| 9,227,194 B2 | 1/2016 | Kume et al. |
| 2004/0013933 A1 | 1/2004 | Korshunov |
| 2006/0166078 A1 | 7/2006 | Chen et al. |
| 2007/0077488 A1 | 4/2007 | Chen et al. |
| 2007/0203541 A1 | 8/2007 | Goetz et al. |
| 2007/0203546 A1 | 8/2007 | Stone et al. |
| 2008/0038643 A1* | 2/2008 | Krehl .............. H01M 4/133 429/322 |
| 2011/0184482 A1 | 7/2011 | Eberman et al. |
| 2012/0078317 A1* | 3/2012 | Wang .............. H01M 2/266 607/5 |
| 2013/0220817 A1 | 8/2013 | Walker et al. |
| 2014/0178750 A1 | 6/2014 | Reddy et al. |
| 2014/0212736 A1 | 7/2014 | Chen et al. |
| 2015/0061176 A1 | 3/2015 | Bruckner et al. |
| 2015/0243967 A1* | 8/2015 | Norton .............. A61N 1/378 600/510 |
| 2015/0311532 A1 | 10/2015 | Chen et al. |
| 2015/0318536 A1 | 11/2015 | Ngaboyamahina et al. |
| 2016/0056459 A1 | 2/2016 | Flitsch et al. |
| 2016/0133932 A1* | 5/2016 | Liang .............. C01B 32/10 429/231.7 |
| 2016/0141718 A1 | 5/2016 | Ye et al. |

* cited by examiner

IMPLANTABLE MEDICAL DEVICE BATTERIES WITH MILLED FLUORINATED CARBON FIBERS, DEVICES, AND METHODS

BACKGROUND

A wide variety of implantable medical devices (IMDs) for delivering a therapy and/or monitoring a physiologic condition have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach, or other organs. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing. For example, electrodes or sensors may be located at a distal portion of the lead. A proximal portion of the lead may be coupled to an implantable medical device housing, which may contain electronic circuitry such as stimulation generation and/or sensing circuitry.

For example, implantable medical devices, such as cardiac pacemakers or implantable cardioverter defibrillators (ICDs), provide therapeutic stimulation to the heart by delivering electrical therapy signals such as pacing pulses, or cardioversion or defibrillation shocks, via electrodes of one or more implantable leads. In some cases, such an implantable medical device may sense intrinsic depolarizations of the heart, and control the delivery of such signals to the heart based on the sensing. When an abnormal rhythm is detected, such as bradycardia, tachycardia or fibrillation, an appropriate electrical signal or signals (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation electrical signals to a patient's heart upon detecting ventricular fibrillation.

Also, implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation or delivery of a pharmaceutical agent, insulin, a pain relieving agent, or an anti-inflammatory agent to a target tissue site within a patient. A medical device may be used to deliver therapy to a patient to treat a variety of symptoms or patient conditions such as chronic pain, tremors, Parkinson's disease, other types of movement disorders, seizure disorders (e.g., epilepsy), urinary or fecal incontinence, sexual dysfunction, obesity, mood disorders, gastroparesis, or diabetes. In some cases, the electrical stimulation may be used for muscle stimulation, e.g., functional electrical stimulation (FES) to promote muscle movement or prevent atrophy. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

SUMMARY

The present disclosure is directed to implantable medical devices, implantable medical device systems that include such implantable medical devices, and implantable medical device batteries, as well as methods of making.

In one embodiment, the present disclosure provides an implantable medical device that includes a battery cell including: an anode; a cathode including fluorinated carbon particles; a separator between the anode and the cathode; and an electrolyte contacting the anode, the cathode, and the separator; wherein greater than 50 percent of the volume (vol-%) of the fluorinated carbon particles have a particle size within a range of 2 microns to 10 microns; and wherein greater than 50% by number have an aspect ratio within a range of 1:1.2 to 1:8.

In another embodiment, the present disclosure provides a non-rechargeable battery that includes: an anode including lithium; a cathode including fluorinated carbon particles and a metal oxide; a separator between the anode and the cathode; and an electrolyte contacting the anode, the cathode, and the separator; wherein greater than 50 vol-% of the fluorinated carbon particles have a particle size within a range of 2 microns to 10 microns; and wherein greater than 50% by number have an aspect ratio within a range of 1:1.2 to 1:8.

In another embodiment, the present disclosure provides an implantable medical device that includes: control electronics for delivering therapy and/or monitoring physiological signals, the control electronics including: a processor; and memory; and an implantable medical device battery operably connected to the control electronics to deliver power to the control electronics. The battery includes: an anode including lithium; a cathode including fluorinated carbon particles; a separator between the anode and the cathode; and an electrolyte contacting the anode, the cathode, and the separator; wherein the cathode comprises a layer on each major surface of the single current collector, wherein the layer includes a mixture comprising a metal oxide and fluorinated carbon particles; wherein greater than 50 vol-% of the fluorinated carbon particles have a particle size within a range of 2 microns to 10 microns; and wherein greater than 50% by number have an aspect ratio within a range of 1:1.2 to 1:8.

In another embodiment, the present disclosure provides an implantable medical device system including: an implantable medical device as described above; and components operably attached to the implantable medical device for delivering therapy and/or monitoring physiological signals.

In another embodiment, the present disclosure provides a method of making a battery cell for use in an implantable medical device. The method includes: providing a fibrous carbon precursor; forming fluorinated carbon fibers from the fibrous carbon precursor; milling the fluorinated carbon fibers to form milled fluorinated carbon fibers; wherein greater than 50 vol-% of the milled fluorinated carbon fibers have a particle size within a range of 2 microns to 10 microns; and wherein greater than 50% by number have an aspect ratio within a range of 1:1.2 to 1:8; forming a cathode comprising the milled fluorinated carbon fibers; providing an anode; providing a separator between the anode and the cathode; providing an electrolyte for activating the anode and the cathode; and combining the cathode, anode, and electrolyte to form a battery cell.

In certain embodiments of the present disclosure, the cathode comprises a silver vanadium oxide and fluorinated carbon particles as described herein.

The term "components for delivering therapy and/or monitoring physiological signals" refers to components of an IMD system that deliver electrical stimulation therapy (e.g., functional electrical stimulation to promote muscle movement, or stimulation to the heart using pacing pulses, cardioversion or defibrillation shocks), deliver a therapeutic agent, monitor physiological signals (e.g., detect ventricular fibrillation), or both deliver and monitor (e.g., detect tachycardia and deliver electrical signals to restore normal rhythm to the heart).

The term "surface area" refers to the area of materials (milled or unmilled fluorinated carbon) as determined by the Brunauer-Emmett-Teller (BET) method.

The term "particle size" refers to the longest dimension of a particle. For a spherical particle, this is the diameter.

The terms "comprises" and variations thereof do not have a limiting meaning where these terms appear in the description and claims.

The terms "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. Thus, for example, a device that comprises "a" capacitors can be interpreted to mean that the device includes "one or more" capacitors.

As used herein, the term "or" is generally employed in its sense including "and/or" unless the content clearly dictates otherwise. The term "and/or" means one or all of the listed elements or a combination of any two or more of the listed elements (e.g., delivering therapy and/or monitoring physiological signals means delivering therapy, monitoring physiological conditions, or doing both monitoring and delivering).

Also herein, all numbers are assumed to be modified by the term "about" and preferably by the term "exactly." Notwithstanding that the numerical ranges and parameters setting forth the broad scope of the disclosure are approximations, the numerical values set forth in the specific examples are reported as precisely as possible. All numerical value, however, inherently contain certain errors necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF FIGURES

The figures presented herein are idealized, not to scale, and are intended to be merely illustrative and non-limiting.

DETAILED DESCRIPTION OF ILLUSTRATIVE EMBODIMENTS

Figure 1:
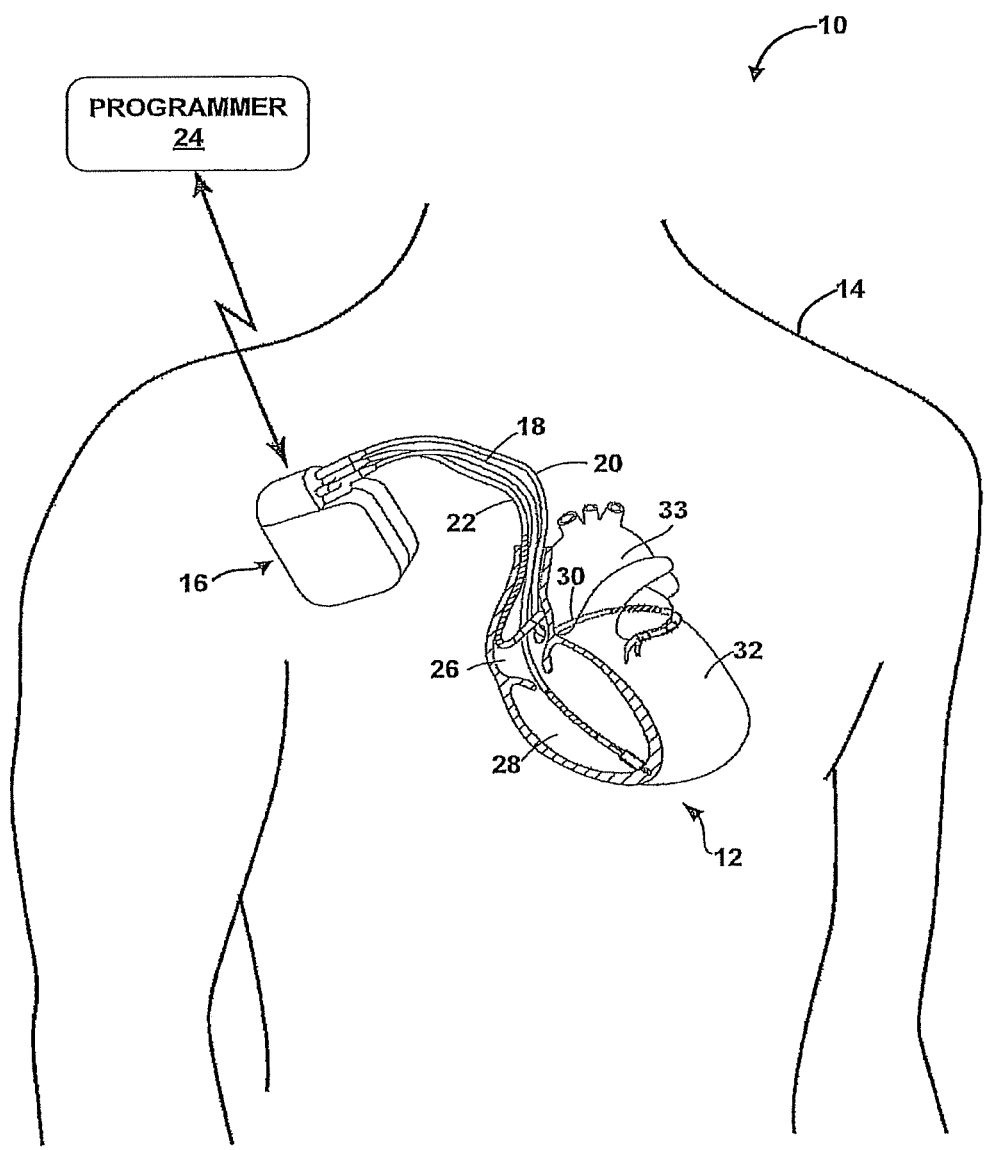
FIG. 1 is a conceptual diagram illustrating an exemplary implantable medical device system (e.g., a therapy system) of the present disclosure.

The present disclosure is directed to implantable medical devices, implantable medical device systems that include such implantable medical devices, and implantable medical device batteries, as well as methods of making.

A wide variety of implantable medical devices (IMDs) for delivering a therapy and/or monitoring a physiologic condition have been clinically implanted or proposed for clinical implantation in patients. Exemplary such IMDs include implantable pulse generators (IPGs), implantable cardioverter defibrillators (ICDs), neurostimulators, or other suitable devices. Of particular importance are implantable cardioverter defibrillators (ICDs).

Whether for electrical stimulation therapy, delivering a therapeutic agent, and/or monitoring a physiological condition, for certain embodiments of the present disclosure it is desirable to have a battery with relatively high power capability and capacity.

A typical battery includes one or more cells that includes an anode, a cathode, a separator between the anode and the cathode; and an electrolyte (typically a liquid electrolyte) contacting the anode, the cathode, and the separator.

A cathode of a battery of the present disclosure includes fluorinated carbon particles. Such fluorinated carbon particles are milled fluorinated carbon fibers. Milling of fluorinated carbon provides several significant performance advantages.

Milling produces cathodes with increased density and improved cathode cohesion, relative to cathodes produced with unmilled fluorinated carbon fibers. In addition, milling produces cathodes with increased volumetric capacity (mAh/cc) relative to cathodes produced with unmilled fluorinated carbon fibers. This is in contrast to fluorinated carbon produced by the fluorination of micron-sized, spherical carbon precursors, which exhibits a lower volumetric capacity.

More specifically, cathodes produced using milled fluorinated carbon fibers have a significantly higher density (e.g., 5-10% higher) than cathodes produced using unmilled fluorinated carbon fibers, which leads to higher volumetric capacity. The percentage improvement depends on the cathode composition.

Also, cathodes produced using milled fluorinated carbon fibers have a significantly higher cohesion strength (e.g., at least 6× higher) than cathodes produced using unmilled fluorinated carbon fibers. This improvement in cohesion improves manufacturability, reduces manufacturing costs, and provides a cathode with higher active (e.g., fluorinated carbon) content, which thereby increases cathode volumetric capacity.

Milled fluorinated carbon fibers generally retain the high specific (gravemetric, mAh/g) capacity of unmilled fluorinated carbon fibers. This is important because any loss in capacity will diminish the benefit of using milled fluorinated carbon fibers. Significantly, fluorinated micron-sized spherical carbons have a lower specific (gravemetric, mAh/g) capacity compared to milled or unmilled fluorinated carbon fibers.

Fluorinated Carbon Particles and Methods of Making

Fluorinated carbon particles used in cathodes of the batteries of the present disclosure are milled fluorinated carbon fibers. In a typical cathode that includes fluorinated carbon particles, greater than 50 vol-% of the fluorinated carbon particles have a particle size within a range of 2 microns to 10 microns. This is also referred to as the D50 particle size distribution. In a typical cathode that includes fluorinated carbon particles, greater than 50% by number of the fluorinated carbon particles have an aspect ratio within a range of 1:1.2 to 1:8.

In certain embodiments of a cathode, greater than 50 vol-% of the fluorinated carbon particles have a particle size within a range of 2 microns to 7 microns, and greater than 50% by number have an aspect ratio within a range of 1:1.2 to 1:4. In certain embodiments of a cathode, greater than 50 vol-% of the fluorinated carbon particles have a particle size within a range of 2 microns to 5 microns, and greater than 50% by number have an aspect ratio within a range of 1:1.3 to 1:2.

In certain embodiments of a cathode, the fluorinated carbon particles have a BET surface area of greater than 300 square meters per gram ($m^2/g$), or greater than 310 $m^2/g$, or greater than 320 $m^2/g$. In certain embodiments of a cathode, the fluorinated carbon particles have a BET surface area of up to 400 $m^2/g$.

In certain embodiments of a cathode, the fluorinated carbon particles have a fluorine atomic weight percentage of at least 61%, or at least 63%, or at least 65%. In certain embodiments of a cathode, the fluorinated carbon particles comprise a fluorine atomic weight percentage of up to 80%, or up to 75%, or up to 71%.

In certain embodiments of a cathode, the fluorinated carbon particles exhibit less than 5% by weight of free carbon. In this context, "free carbon" refers to elemental carbon in an uncombined state (i.e., unreacted carbon) as determined by X-ray diffraction (XRD).

In certain embodiments, fluorinated carbon particles are milled fluorinated carbon fibers formed from fluorinated carbon fibers as described in U.S. Pat. No. 7,824,805 (Howard et al.). Typically, such fluorinated carbon is referred to as carbon monofluoride, carbon fluoride, polycarbon monofluoride, $CF_x$, or graphite fluoride. It is a solid, structural, non-stoichiometric fluorocarbon of empirical formula $CF_x$, wherein x is 0.01 to 1.9, preferably 0.1 to 1.5, and more preferably 1.1. One commercial form of carbon monofluoride is $(CF_x)_n$ where 0<x<1.25 (and n is the number of monomer units in the polymer, which can vary widely).

Generally, production of $CF_x$ involves an exemplary chemical reaction such as:

$$F_2+(x+y+z)C \rightarrow xCF_{1.1}+yC+z(CF_{n\geq 2})$$

where x, y, and z are numerical values that may be positive integers or positive rational numbers. In this reaction, fluorine and carbon react to form $CF_{1.1}$. Unreacted carbon and impurities are by-products of the chemical reaction, which are preferably minimized during production of $CF_x$. It is desirable to achieve a weight percentage of fluorine greater than or equal to 61% in $CF_x$ while reducing impurities. Preferably, greater than or equal to 63%, or greater than or equal to 65%, of fluorine exists in the $CF_x$. Purity, crystallinity, and particle shape, particularly of the carbon precursor (prior to forming fluorinated carbon fibers) and the fluorinated carbon fibers (prior to milling) are also properties to consider in the selection of carbon monofluoride.

Suitable fluorinated carbon fibers that are milled to form fluorinated carbon particles are described in greater detail in U.S. Pat. No. 7,824,805 (Howard et al.). The fluorinated carbon fibers and the fluorinated carbon particles derived therefrom have less than 1% by weight of $CF_2$ and $CF_3$, and that exhibit an XRD pattern comprising: an area ratio of a 110 peak relative to a 001 peak of ≥4.52%; and a position of a 001 peak centered at ≥13.06° $2\theta_{001}$ Cu K$\alpha$.

In certain embodiments, the fluorinated carbon fibers are formed from a fibrous carbon precursor that includes greater than 95% by weight of carbon, or greater than 99% by weight of carbon, as determined by a combustion technique. In certain embodiments, the fibrous carbon precursor comprises polyacrylonitrile (PAN).

As described in U.S. Pat. No. 7,824,805 (Howard et al.), purity and crystallinity of the carbon precursor affect the percentage by weight of fluorine in $CF_x$. In terms of purity, it is desirable that the carbon precursor has less than or equal to 1% of elemental impurities. In addition to purity, low crystallinity in the carbon precursor is desirable since it allows the carbon precursor to be fully fluorinated at lower temperatures (e.g. less than or equal to 400 Celsius (° C.)). PAN or rayon-based carbon fibers that possess high purity and low crystallinity, can be homogeneously fluorinated to yield a desired fibrous $CF_x$ product. In addition, high purity fibrous carbons with high crystallinity may also be fully fluorinated at high temperatures (e.g., temperatures greater than 400° C.) and may yield desirable properties. Non-fibrous carbon samples, with high purity and low crystallinity, can be fully fluorinated to yield a desired product with homogeneous fluorination. Similarly, it is likely that non-fibrous carbon with high purity and high crystallinity can be fully fluorinated at high temperatures (e.g., temperatures greater than 400° C.) and may yield desirable properties.

In certain embodiments, the present disclosure provides a method of making a battery cell for use in an implantable medical device. The method includes: providing a fibrous carbon precursor (e.g., polyacrylonitrile); forming fluorinated carbon fibers from the fibrous carbon precursor (e.g., as described in U.S. Pat. No. 7,824,805 (Howard et al.)); milling the fluorinated carbon fibers to form milled fluorinated carbon fibers; wherein greater than 50 vol-% of the milled fluorinated carbon fibers have a particle size within a range of 2 microns to 10 microns; and wherein greater than 50% by number have an aspect ratio within a range of 1:1.2 to 1:8.

In certain embodiments, milling the fluorinated carbon fibers includes ball milling, jet milling, attritor milling, and/or other particle size reduction processes.

In certain embodiments, milling the fluorinated carbon fibers to form milled fluorinated carbon fibers involves ball milling the fluorinated carbon fibers. In certain embodiments, ball milling is performed with a ball to fluorinated carbon fiber volume loading ratio of 1:2.5, and with a container (jar) to fluorinated carbon fiber volumetric loading ratio of 3:1.

In certain embodiments, milling the fluorinated carbon fibers to form milled fluorinated carbon fibers involves ball milling the fluorinated carbon fibers for at least 1 hour, or at least 4 hours, or at least 5 hours, or at least 6 hours, or at least 7 hours, or at least 8 hours.

In certain embodiments, milling the fluorinated carbon fibers to form milled fluorinated carbon fibers involves ball milling the fluorinated carbon fibers for up to 16 hours.

In certain embodiments, milling the fluorinated carbon fibers to form milled fluorinated carbon fibers includes ball milling the fluorinated carbon fibers at a frequency of 100 revolutions per minute (rpm) to 400 rpm.

The method of making a battery cell for use in an implantable medical device further includes forming a cathode comprising the milled fluorinated carbon fibers; providing an anode; providing a separator between the anode and the cathode; providing an electrolyte for activating the anode and the cathode; and combining the cathode, anode, and electrolyte to form a battery cell. The techniques for implementing these steps are well known to those of skill in the art.

Exemplary Implantable Medical Device Batteries

Although certain materials described herein are rechargeable, implantable medical device batteries of the present disclosure are preferably primary (i.e., non-rechargeable) batteries. A typical battery includes a case, a liner, and an electrode assembly. The liner surrounds the electrode assembly to prevent the electrode assembly from contacting the inside of the case. The electrode assembly includes one or more electrochemical cells, wherein each electrochemical cell includes an anode and a cathode with one or more separators there between, and an electrolyte to facilitate ionic transport and form a conductive pathway between the anode and cathode.

A typical battery includes one or more cells that includes an anode, a cathode, a separator between the anode and the cathode; and an electrolyte (typically a liquid electrolyte) contacting the anode, the cathode, and the separator. The separator insulates an anode from a cathode. The electrolyte creates a conductive path between the anode and the cathode and serves as a medium for migration of ions between the anode and the cathode during discharge of the cell.

Cathodes and anodes of batteries of the present disclosure may have a variety of shapes. Typically, they are in the form of monolithic, plates, or coils. For example, an electrode (cathode or anode) is typically a thin coating, sheet, or foil of the active material disposed on one or both major surfaces of a thin film of a current collector (e.g., nickel, copper, aluminum, titanium, gold, platinum, tantalum, stainless steel, or another conductive metal that is corrosion-resistant when associated with the active material). An anode, cathode, and separator can be combined in a variety of structures, including, for example, spiral wound form, stacked plate form, serpentine form, or medium-rate battery, as disclosed, for example, in U.S. Pat. No. 5,439,760 (Howard et al.), U.S. Pat. Appl. Pub. No. 2006/0166078 (Chen et al.), and U.S. Pat. No. 5,716,729 (Sunderland et al.).

Preferably, each electrode includes one current collector (i.e., one single layer of a current collector). That is, for certain preferred embodiments, for a coiled electrode, each of the cathode and anode includes one current collector. For a stacked plate electrode assembly, however, in any one electrode plate, there is one current collector or one single layer of a current collector, which are electrically connected to each other to form a "single" current collector for the combined set of electrode plates.

Typically, anodes of IMD batteries are formed of an active material that includes lithium, which can be in metallic or ionic form (typically, metallic form). It may also include other materials, particularly those selected from Group IA (i.e., Group 1, the alkali metal group), and Group IIA (i.e., Group 2, the alkaline earth group) of the periodic table of elements (e.g., sodium, potassium, etc.). The anode can include mixtures, alloys (e.g., Li—Al alloy), or intermetallic compounds (e.g., Li—Si, Li—B, Li—Si—B etc.) of the elements of Groups IA, IIA, or IIIA (i.e., Group 13, e.g., aluminum, gallium) of the periodic table with each other or with other elements of the periodic table.

Cathodes of IMD batteries of the present disclosure are formed of an active material that includes the fluorinated carbon particles, and preferably one or more metal oxides. Such metal oxides may include one or more different metals (e.g., the active material can include mixed metal oxides). The cathode material can also include two or more different materials, which can be in admixture or in layers, or both.

Exemplary metal oxides for use in the cathode active material include $Ag_2O$, $Ag_2O_2$, $CuF$, $Ag_2CrO_4$, $MnO_2$, $V_6O_{13}$, silver vanadium oxide (e.g., $AgV_2O_5$, $Ag_2V_4O_{11}$, $Ag_{0.35}V_2O_{5.8}$, $Ag_{0.74}V_2O_{5.37}$, $AgV_4O_{5.5}$), copper silver vanadium oxide (e.g., $Cu_{0.16}Ag_{0.67}V_2O_{5.5}$ or $Cu_{0.5}Ag_{0.5}V_2O_{5.75}$), $V_2O_5$, copper oxide, copper vanadium oxide, or combinations thereof. Combinations of such materials can be used if desired.

In certain embodiments, $MnO_2$ is a useful active cathode material. Examples of $MnO_2$-containing cathodes are described in U.S. Pat. No. 5,344,431 (Merritt et al.) and U.S. Pat. No. 5,474,858 (Merritt).

Preferred metal oxides are the various materials that include silver vanadates, referred to generally as "silver vanadium oxide" or "SVO." SVO is capable of being synthesized using a variety of methods. Methods of synthesis generally fall within two categories, depending on the type of chemical reaction that produces the SVO. SVO can be synthesized using a decomposition reaction, resulting in decomposition-produced SVO (DSVO). Alternatively, SVO can be synthesized using a combination reaction, resulting in combination-produced SVO (CSVO). Regardless of how it is made, SVO can be formed in a variety of different structural phases (e.g., β, γ, and ε) and have a variety of different crystalline forms. A particularly preferred metal oxide is $Ag_2V_4O_{11}$, which is prepared by the addition reaction described in U.S. Pat. No. 5,221,453 (Crespi) and U.S. Pat. No. 6,130,005 (Crespi et al.).

In certain embodiments, a cathode includes a metal oxide, such as $MnO_2$ or silver vanadium oxide, along with the fluorinated carbon particles (i.e., milled fluorinated carbon fibers). This is referred to herein as a mixture of actives. In certain embodiments, the fluorinated carbon particles and metal oxide, particularly silver vanadium oxide, are present in the cathode in amounts within a range of 0.3:1 to 10:1, or within a range of 1:1 to 10:1, or within a range of 0.3:1 to 3.5:1.

In certain embodiments, the actives, fluorinated carbon particles and metal oxide, particularly silver vanadium oxide, are present in the cathode in a total amount of 80 percent by weight (wt-%) to 96 wt-%, or 85 wt-% to 92 wt-%, or 88 wt-% to 92 wt-%, based on the total weight of the cathode.

The cathode material typically also includes a conductivity enhancer and a binder.

The conductivity enhancer is typically a conductive carbon, such as carbon black, acetylene black, carbon nanotubes, graphene, and/or graphite, although other metallic powders can be used such as aluminum, titanium, nickel, and stainless steel. Various combinations of such conductivity enhancers can be used if desired. The amount of conductive enhancer is typically at least 0.1 wt-%, and typically no more than 10 wt-%, based on the total weight of the dry cathode mix (without solvent).

The binder can be carboxy methyl cellulose (CMC), styrene-butadiene rubber (SBR), polyvinylidene difluoride (PVDF), polytetrafluoroethylene (PTFE), or combinations thereof. Preferred binders are PTFE and PVDF. A more preferred binder is PTFE. The amount of binder is typically at least 1 wt-%, and typically no more than 10 wt-%, based on the total weight of the dry cathode mix (without solvent).

The current collectors used in the electrodes of IMD batteries of the present disclosure are of the type used conventionally. Generally, they are metal films or foils, such as aluminum, titanium, nickel, copper, or another conductive metal that is corrosion-resistant when associated with the active anode material. They may be primed or unprimed. They may be perforated or not. The thicknesses of the current collectors are typically at least 0.0001 inch, and more often at least 0.020 inch.

The separators used in electrochemical cells of IMD batteries of the present disclosure are selected to electrically insulate the anode from the cathode. Conventional materials can be used. The material is generally wettable by the cell electrolyte, sufficiently porous to allow the electrolyte to flow through separator material, and maintains physical and chemical integrity within the cell during operation. Examples of suitable separator materials include, but are not limited to, fluoropolymeric fabrics, polytetrafluoroethylene (PTFE), ceramics, non-woven glass, glass fiber material, polypropylene, and polyethylene. For example, the separator can include microporous polyethylene (PE) or polypropylene (PP) and/or a layer of non-woven polypropylene or polyethylene laminated to it. As described in U.S. Pat. Appl. Pub. No. 2006/0166078 (Chen et al.), a separator can consist of three layers, for example, having a polyethylene layer sandwiched between two layers of polypropylene. The polyethylene layer has a lower melting point than the polypropylene layers and provides a shut-down mechanism in case of cell over-heating.

The electrolyte includes a liquid organic electrolyte, which typically includes an organic solvent in combination with an ionizing solute. The organic solvent can be, for example, diethylcarbonate, dimethylcarbonate, dipropylcarbonate, diisopropylcarbonate, di-tert-butylcarbonate, dibutylcarbonate, diphenylcarbonate, dicyclopentylcarbonate, ethylenecarbonate, butylenecarbonate, 3-methyl-2-oxazolidone, sulfolane, tetrahydrofuran (THF), methyl-substituted tetrahydrofuran, 1,3-dioxolane, propylene carbonate (PC), ethylene carbonate, gamma-butyrolactone, ethylene glycol sulfite, dimethylsulfite, dimethyl sulfoxide, 1,2-dimethoxyethane, dimethyl isoxazole, dioxane, ethyl methyl carbonate, methyl formate, diglyme, glyme, acetonitrile, N-methyl-2-pyrrolidone (NMP), solvents of the type disclosed in U.S. Pat. No. 6,017,656 (Crespi et al.), or the like, or mixtures thereof. The ionizing solute can be a simple or soluble salt or mixtures thereof, for example, an alkali metal salt (e.g., $LiBF_4$, $LiAsF_6$, $LiPF_6$, $LiClO_4$, $LiN(SO_2CF_3)_2$, $LiC(SO_2CF_3)_3$, $LiSbF_6$, $LiO_2$, $LiAlCl_4$, $LiGaCl_4$, $LiSCN$, $LiO_3SCF_3$, $LiC_6F_5SO_3$, $LiO_2CCF_3$, $LiSO_6F$, $LiB(C_6H_5)_4$, $LiCF_3SO_3$, and mixtures thereof), which will produce an ionically conductive solution when dissolved in one or more solvents. For example, the electrolyte can include a lithium salt (e.g., 1.0M $LiClO_4$ or $LiPF_6$ or $LiAsF_6$) in a 50/50 mixture of propylene carbonate and 1,2-dimethoxyethane. A preferred electrolyte is 1.0M $LiAsF_6$ in a mixture of 50 volume percent (vol-%) propylene carbonate (PC) and 50 vol-% 1,2-dimethoxyethane (DME).

Exemplary Implantable Medical Devices and Systems

FIG. 1 is a conceptual diagram illustrating an exemplary implantable medical device system (e.g., a therapy system) 10 that may be used to provide therapy to heart 12 of patient 14. Patient 14 ordinarily, but not necessarily, will be a human. Therapy system 10 includes IMD 16, which is coupled to leads 18, 20, 22, and programmer 24. IMD 16 may be, for example, an implantable pacemaker, cardioverter, and/or defibrillator that provides electrical signals to heart 12 via electrodes coupled to one or more of leads 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation by employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may, for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, by which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radio frequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
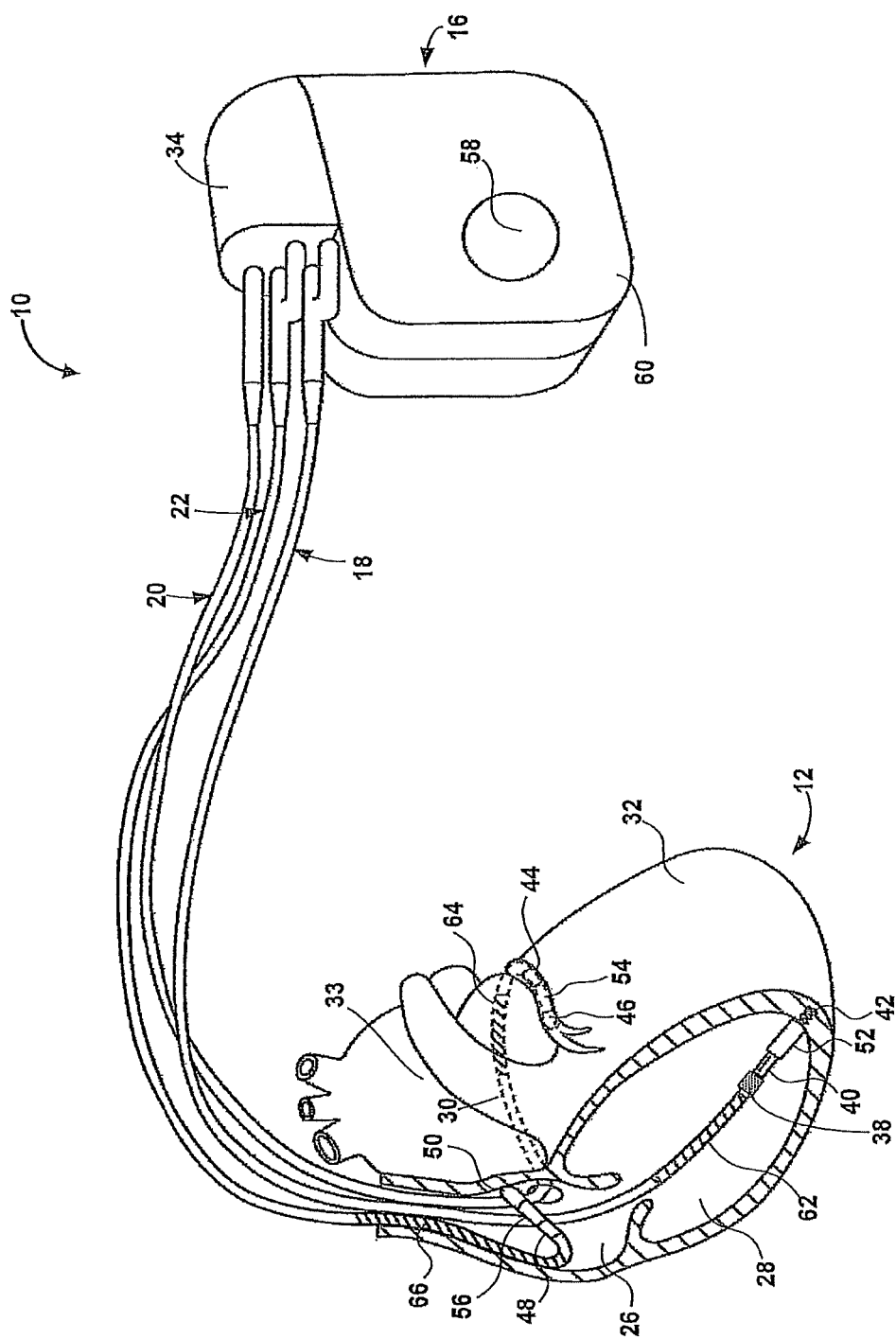
FIG. 2 is a conceptual diagram illustrating an IMD and leads of a therapy system of the present disclosure in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins, or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 38 may respond to an absolute pressure inside right ventricle 28, and may be, for example, a capacitive or piezoelectric absolute pressure sensor. In other examples, pressure sensor 38 may be positioned within other regions of heart 12 and may monitor pressure within one or more of the other regions of heart 12, or may be positioned elsewhere within or proximate to the cardiovascular system of a patient to monitor cardiovascular pressure associated with mechanical contraction of the heart.

Electrodes 40, 44, 48 may take the form of ring electrodes, and electrodes 42, 46, 50 may take the form of extendable helix tip electrodes mounted retractably within insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to respective one of the electrical contacts on the proximal end of leads 18, 20, 22.

Electrodes 40, 42, 44, 46, 48, 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48, 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, 50 may be used for unipolar sensing or pacing in combination with housing electrode 58.

As described with reference to FIG. 4, housing 60 may enclose a stimulation generator that generates cardiac pacing pulses and/or defibrillation and/or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes. In addition, in some examples, pressure sensor 38 may be self-contained device that is implanted within heart 12, such as within the septum separating right ventricle 28 from left ventricle 32, or the septum separating right atrium 26 from left atrium 33. In such an example, pressure sensor 38 may wirelessly communicate with IMD 16.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. As another example, other examples of therapy systems may include a single lead that extends from IMD 16 into right atrium 26 or right ventricle 28, or two leads that extend into a respective one of the right ventricle 28 and right atrium 26. An example of this type of therapy system is shown in FIG. 3.

Figure 3:
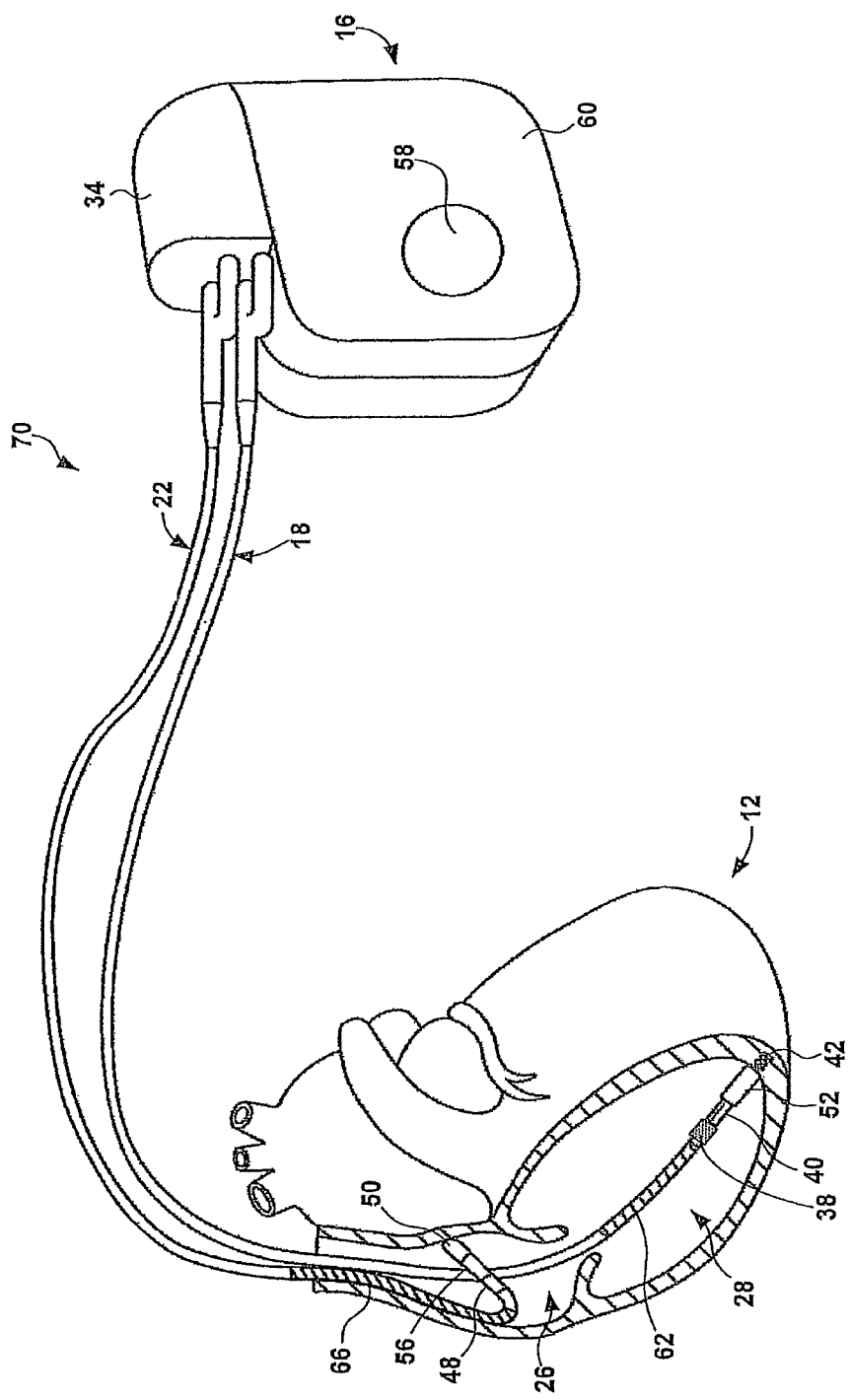
FIG. 3 is a conceptual diagram illustrating another example of an implantable medical device system (e.g., a therapy system) of the present disclosure.

FIG. 3 is a conceptual diagram illustrating another example of an implantable medical device system (e.g., a therapy system) 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and/or pacing pulses to heart 12.

Figure 4:
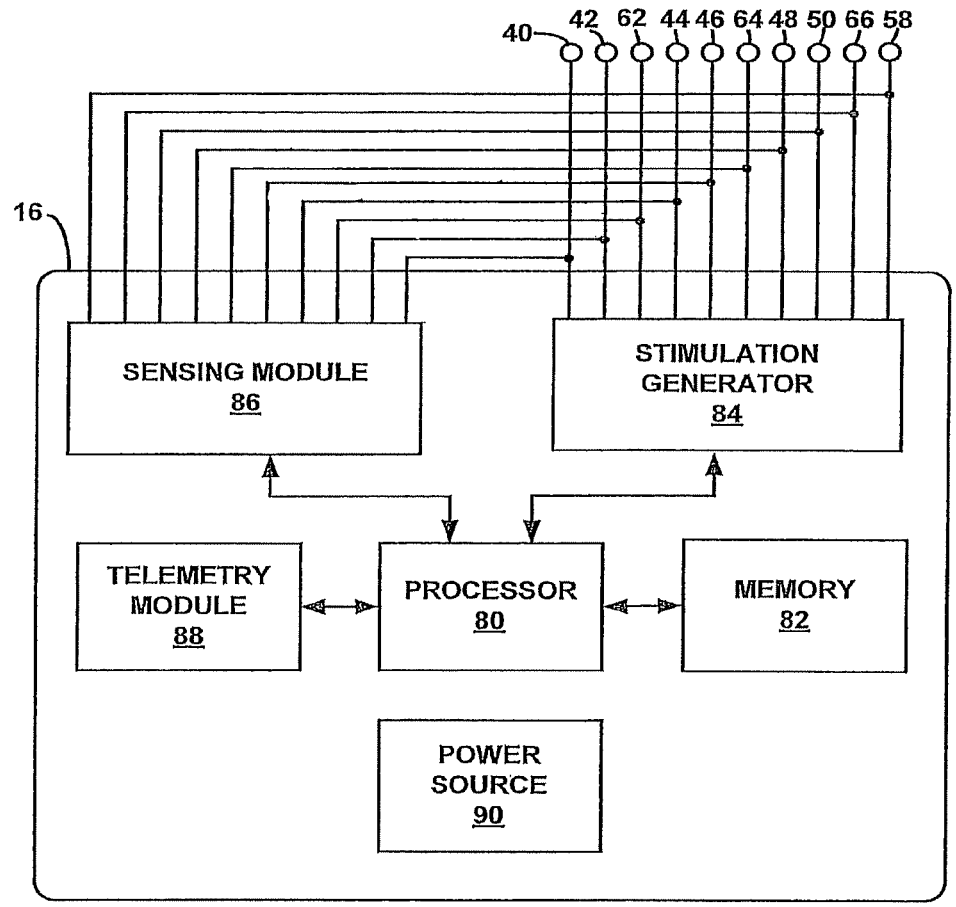
FIG. 4 provides further detail of an exemplary IMD of the present disclosure.

FIG. 4 is a functional block diagram of one example configuration of IMD 16, which includes processor 80, memory 82, stimulation generator 84, sensing module 86, telemetry module 88, and power source 90. Herein, for IMD 16, the processor 80, memory 82, stimulation generator 84, sensing module 86, and telemetry module 88 are collectively referred to as "control electronics." Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. Processor 80 controls stimulation generator 84 to deliver stimulation therapy to heart 12 according to a selected one or more of therapy programs, which may be stored in memory 82. Specifically, processor 80 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via electrodes 40, 44, 48 (e.g., ring electrodes) coupled to leads 18, 20, 22, respectively, and/or electrodes 42, 46, 50 (e.g., helical electrodes) of leads 18, 20, 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks and/or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64, 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprises an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 (Keimel et al.). Other amplifiers may also be used. Furthermore, in some examples, one or more of the sensing channels of sensing module 86 may be selectively coupled to housing electrode 58, or elongated electrodes 62, 64, 66, with or instead of one or more of electrodes 40, 42, 44, 46, 48, 50, e.g., for unipolar sensing of R-waves or P-waves in any of chambers 26, 28, 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR, and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves. Stimulation generator 84 may include pacer output circuits that are coupled, e.g., selectively by a switching module, to any combination of electrodes 40, 42, 44, 46, 48, 50, 58, 62, 64, 66 appropriate for delivery of a bipolar or unipolar pacing pulse to one of the chambers of heart 12. Processor 80 may reset the escape interval counters upon the generation of pacing pulses by stimulation generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 80 may identify the presence of a tachyarrhythmia episode, such as a ventricular fibrillation episode, a ventricular tachycardia episode, or a non-sustained tachycardia (NST) episode.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 (Olson et al.) or in U.S. Pat. No. 5,755,736 (Gillberg et al.). Other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 80 may determine that the tachyarrhythmia is present.

If processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by stimulation generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver defibrillation shocks to heart 12, stimulation generator 84 may include a high voltage charge circuit and a high voltage output circuit. In the event that generation of a cardioversion or defibrillation shock is required, processor 80 may employ the escape interval counter to control timing of such cardioversion and defibrillation shocks, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by stimulation generator 84 is controlled by the cardioversion/defibrillation control module of processor 80. Following delivery of the fibrillation or tachycardia therapy, processor 80 may return stimulation generator 84 to a cardiac pacing function and await the next successive interrupt due to pacing or the occurrence of a sensed atrial or ventricular depolarization.

Stimulation generator 84 may deliver cardioversion or defibrillation shocks with the aid of an output circuit that determines whether a monophasic or biphasic pulse is delivered, whether housing electrode 58 serves as cathode or anode, and which electrodes are involved in delivery of the cardioversion or defibrillation shocks. Such functionality may be provided by one or more switches or a switching module of stimulation generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac episodes that sensing module 86 detects, and transmit the marker codes to programmer 24. An example pacemaker with marker-channel capability is described in U.S. Pat. No. 4,374,382 (Markowitz).

The various components of IMD 16 are coupled to power source 90, which includes a non-rechargeable (or "primary") battery as described in greater detail herein below.

Figure 5:
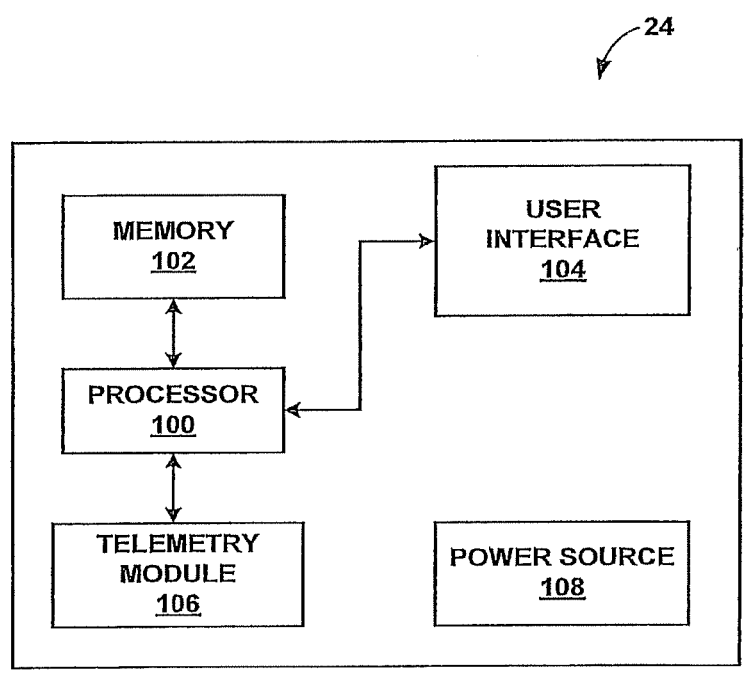
FIG. 5 is block diagram of an exemplary programmer used with an implantable medical device of the present disclosure.

FIG. 5 is block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 108 delivers operating power to the components of programmer 24. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other embodiments, traditional primary batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Referring again to FIG. 4, processor 80 of IMD 16 may detect a tachyarrhythmia episode, such as a ventricular fibrillation, ventricular tachycardia, fast ventricular tachyarrhythmia episode, or a NST episode, based on electrocardiographic activity of heart 12 that is monitored via sensing module 86. For example, sensing module 86, with the aid of at least some of the electrodes 40, 42, 44, 46, 48, 50, 58, 62, 64, 66 (shown in FIGS. 1-2), may generate an electrocardiogram (ECG) or electrogram (EGM) signal that indicates the electrocardiographic activity. Alternatively, sensing module 86 may be coupled to sense electrodes that are separate from the stimulation electrodes that deliver electrical stimulation to heart 12 (shown in FIGS. 1-3), and may be coupled to one or more different leads than leads 18, 20, 22 (shown in FIGS. 1-2). The ECG signal may be indicative of the depolarization of heart 12.

For example, as previously described, in some examples, processor 80 may identify the presence of a tachyarrhythmia episode by detecting a threshold number of tachyarrhythmia events (e.g., R-R or P-P intervals having a duration less than or equal to a threshold). In some examples, processor 80 may also identify the presence of the tachyarrhythmia episode by detecting a variable coupling interval between the R-waves of the heart signal.

Figure 6:
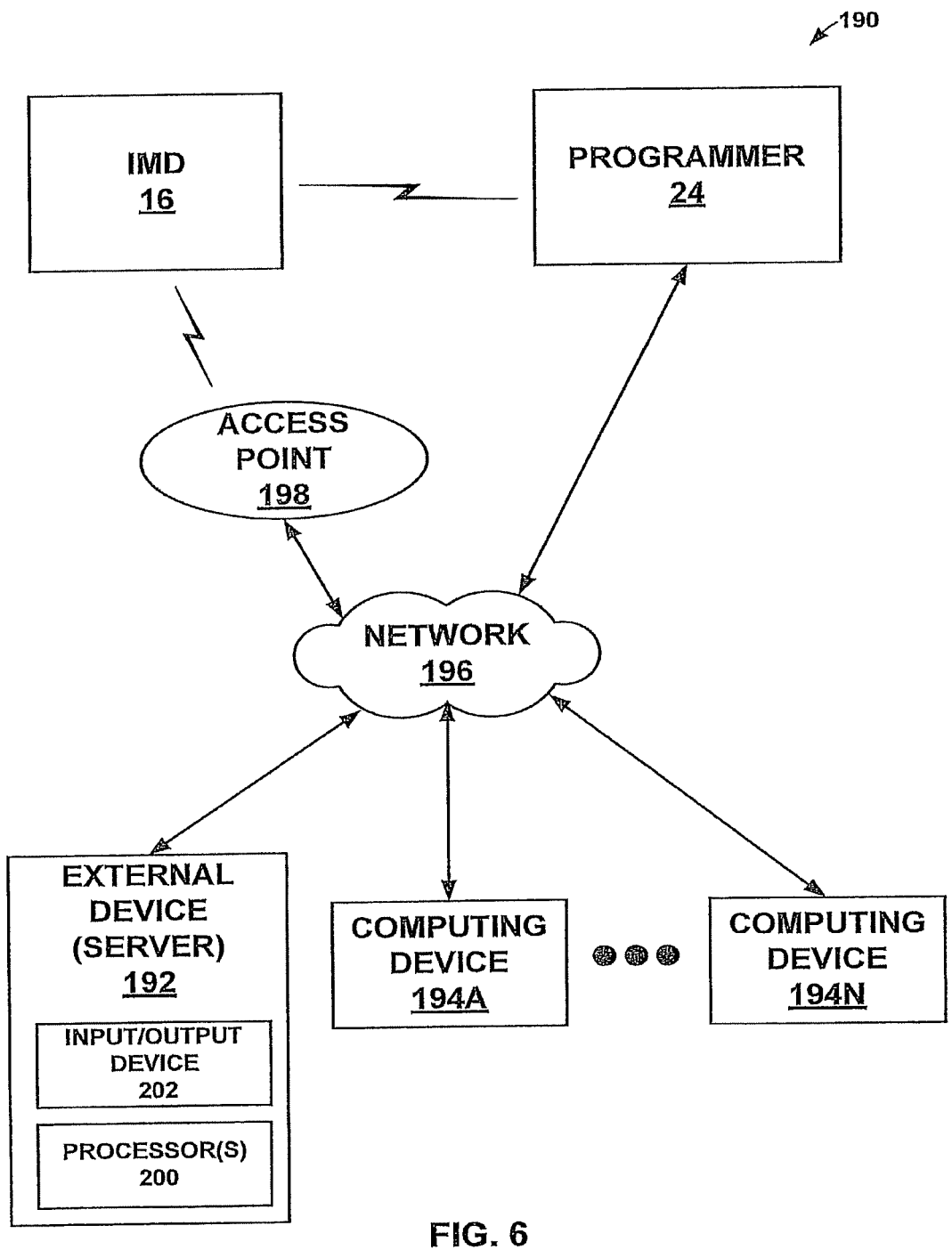
FIG. 6 is a block diagram illustrating a system that includes an external device, such as a server, and one or more computing devices coupled to an IMD of the present disclosure, and a programmer via a network 196.

FIG. 6 is a block diagram illustrating a system 190 that includes an external device 192, such as a server, and one or more computing devices 194A-194N that are coupled to IMD 16 and programmer 24 shown in FIG. 1 via a network 196, according to one embodiment. In this embodiment, IMD 16 uses its telemetry module 88 to communicate with programmer 24 via a first wireless connection, and to communicate with an access point 198 via a second wireless connection. In the example of FIG. 6, access point 198, programmer 24, external device 192, and computing devices 194A-194N are interconnected, and able to communicate with each other, through network 196. In some cases, one or more of access point 198, programmer 24, external device 192, and computing devices 194A-194N may be coupled to network 196 through one or more wireless connections. IMD 16, programmer 24, external device 192, and computing devices 194A-194N may each comprise one or more processors, such as one or more microprocessors, DSPs, ASICs, FPGAs, programmable logic circuitry, or the like, that may perform various functions and operations, such as those described herein.

Access point 198 may comprise a device that connects to network 196 via any of a variety of connections, such as telephone dial-up, digital subscriber line (DSL), or cable modem connections. In other examples, access point 198 may be coupled to network 196 through different forms of connections, including wired or wireless connections. In some examples, access point 198 may communicate with programmer 24 and/or IMD 16. Access point 198 may be co-located with patient 14 (e.g., within the same room or within the same site as patient 14) or may be remotely located from patient 14. For example, access point 198 may be a home monitor that is located in the patient's home or is portable for carrying with patient 14.

During operation, IMD 16 may collect, measure, and store various forms of diagnostic data. In certain cases, IMD 16 may directly analyze collected diagnostic data and generate any corresponding reports or alerts. In some cases, however, IMD 16 may send diagnostic data to programmer 24, access point 198, and/or external device 192, either wirelessly or via access point 198 and network 196, for remote processing and analysis.

In some cases, IMD 16 and/or programmer 24 may combine all of the diagnostic data into a single displayable lead integrity report, which may be displayed on programmer 24. The lead integrity report contains diagnostic information concerning one or more electrode leads that are coupled to IMD 16, such as leads 18, 20, or 22. A clinician or other trained professional may review and/or annotate the lead integrity report, and possibly identify any lead-related conditions.

In another example, IMD 16 may provide external device 192 with collected diagnostic data via access point 198 and network 196. External device 192 includes one or more processors 200. In some cases, external device 192 may request such data, and in some cases, IMD 16 may automatically or periodically provide such data to external device 192. Upon receipt of the diagnostic data via input/output device 202, external device 192 is capable of analyzing the data and generating reports or alerts upon determination that there may be a possible condition with one or more of leads 18, 20, and 22. For example, one or more of leads 18, 20, and 22 may experience a condition related to a lead fracture or an insulation breach.

In one embodiment, external device 192 may combine the diagnostic data into a lead integrity report. One or more of computing devices 194A-194N may access the report through network 196 and display the report to users of computing devices 194A-194N. In some cases, external device 192 may automatically send the report via input/output device 202 to one or more of computing devices 194A-194N as an alert, such as an audio or visual alert. In some cases, external device 192 may send the report to another device, such as programmer 24, either automatically or upon request. In some cases, external device 192 may display the report to a user via input/output device 196.

In one embodiment, external device 192 may comprise a secure storage site for diagnostic information that has been collected from IMD 16 and/or programmer 24. In this embodiment, network 196 may comprise an Internet network, and trained professionals, such as clinicians, may use computing devices 194A-194N to securely access stored diagnostic data on external device 192. For example, the trained professionals may need to enter usernames and passwords to access the stored information on external device 192. In one embodiment, external device 192 may be a CareLink server provided by Medtronic, Inc., of Minneapolis, Minn.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Figure 7A:
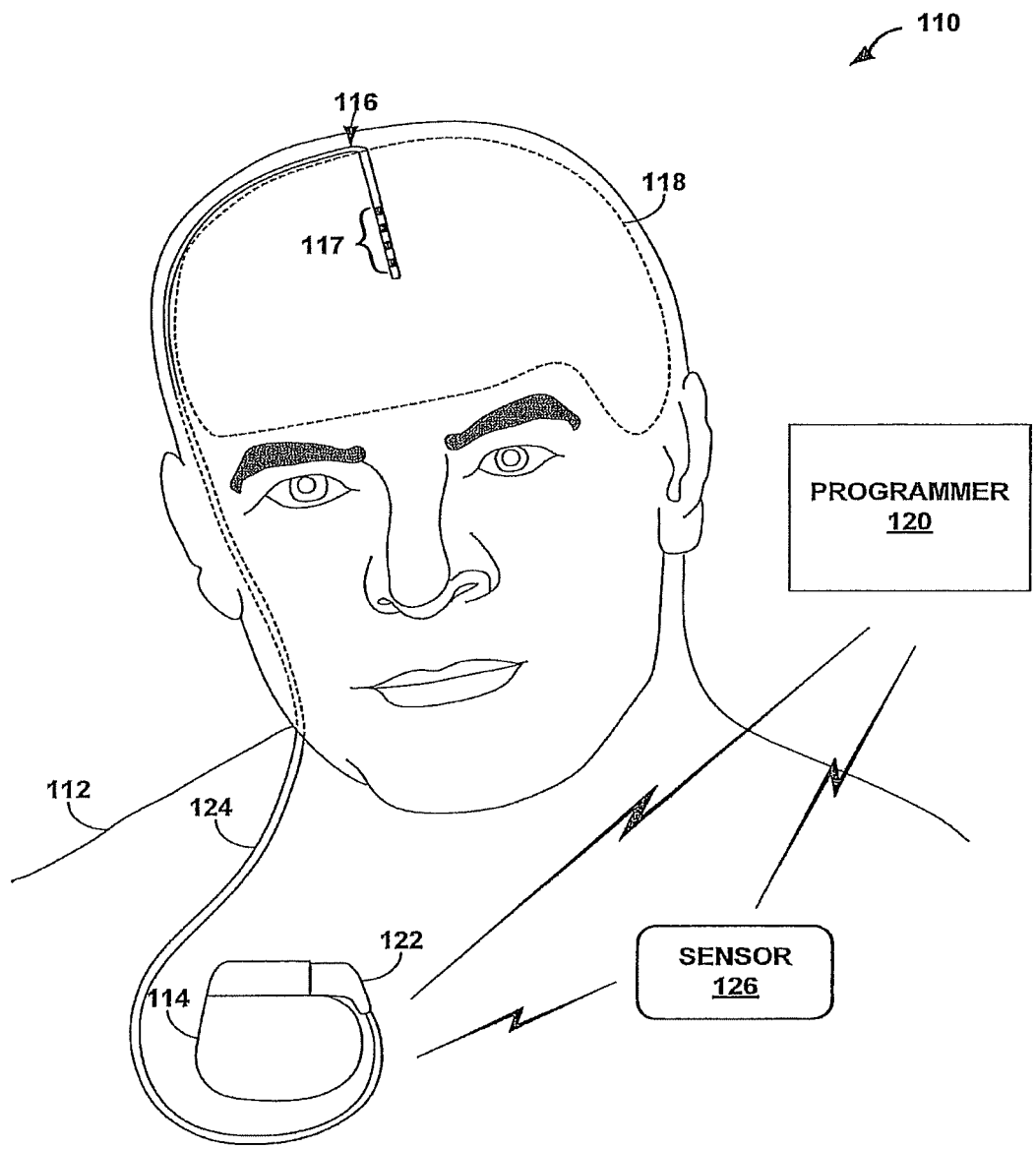
FIG. 7A is a conceptual diagram illustrating an exemplary implantable medical device system (e.g., a therapy system) that provides electrical stimulation therapy to a patient according to the present disclosure.

FIG. 7A is a conceptual diagram illustrating an exemplary implantable medical device system (e.g., a therapy system) 110 that provides electrical stimulation therapy to patient 112. Therapy system 110 includes IMD 114 and medical lead 116. In the example shown in FIG. 7A, IMD 114 provides deep brain stimulation (DBS) to brain 118 of patient 112. Lead 116 is implanted within patient 112 such that one or more electrodes 117 carried by lead 116 are located proximate to a target tissue site within brain 118. IMD 114 provides electrical stimulation to regions within brain 118 in order to manage a condition of patient 112, such as to mitigate the severity or duration of the patient condition. In some examples, more than one lead 116 may be implanted within brain 118 of patient 112 to provide stimulation to multiple anatomical regions of brain 118. As shown in FIG. 7A, system 110 may also include a programmer 120, which may be a handheld device, portable computer, or workstation that provides a user interface to a clinician or other user. The clinician may interact with the user interface to program stimulation parameters.

DBS may be used to treat various patient conditions, such as, but not limited to, seizure disorders (e.g., epilepsy), pain, migraine headaches, psychiatric disorders (e.g., mood or anxiety disorders), movement disorders (e.g., essential tremor or Parkinson's disease), Huntington's disease, and other neurodegenerative disorders. The anatomic region within patient 112 that serves as the target tissue site for stimulation delivered by IMD 114 may be selected based on the patient condition. For example, stimulating an anatomical region, such as the substantia nigra, in brain 118 may reduce the number and magnitude of tremors experienced by patient 112. Other target anatomical regions for treatment of movement disorders may include the subthalamic nucleus, globus pallidus interna, ventral intermediate, and zona inserta. Anatomical regions such as these may be targeted by the clinician during implantation of lead 116. In other words, the clinician may attempt to position lead 116 within or proximate to these target regions within brain 118.

DBS lead 116 may include one or more electrodes 117 placed along the longitudinal axis of lead 116. In some examples, electrodes 117 may include at least one ring electrode that resides along the entire circumference of lead 116. Electrical current from the ring electrodes propagates in all directions from the active electrode. The resulting stimulation field reaches anatomical regions of brain 118 within a certain distance in all directions. The stimulation field may reach the target anatomical region, but the stimulation field may also affect non-target anatomical regions and produce unwanted side effects. In other examples, lead 116 may include a complex electrode array geometry that includes segmented or partial ring electrodes in addition to or instead of ring electrodes. The electrodes in a complex electrode array may be located at different axial and angular positions around the circumference of the lead, as well as at different longitudinal positions (i.e., along the longitudinal axis of lead 116). A complex electrode array geometry may be useful for customizing the stimulation field and provide improved therapy while decreasing side effects. For example, with a complex electrode array, electrodes may be selected along the longitudinal axis of lead 116 as well as along the circumference of lead 116. Activating selective electrodes of lead 116 can produce customizable stimulation fields that may be directed to a particular side of lead 116 in order to isolate the stimulation field around the target anatomical region of brain 118. In this manner, specific electrodes of the complex electrode array geometry may be selected to produce a stimulation field at desired portions of the circumference instead of always producing a stimulation field around the entire circumference of the lead, as with some ring electrodes.

Producing irregular stimulation fields with a lead 116 with a complex electrode geometry may allow therapy system 110 to more effectively treat certain anatomical regions of brain 118. In some cases, a therapy system 110 including lead 116 with a complex electrode array may also help reduce or eliminate side effects from more spherical stimulation fields produced by a conventional array of ring electrodes. The center of the stimulation field may be moved away from lead 116 to avoid unwanted stimulation or compensate for inaccurately placed leads.

In the example shown in FIG. 7A, lead 116 is coupled to IMD 114 via connector 122, which defines a plurality of electrical contacts for electrically coupling electrodes 117 to a stimulation generator within IMD 114. Lead 116 is indirectly coupled to connector 122 with the aid of lead extension 124. In some examples, lead 116 may be directly coupled to connector 122 without the aid of extension 124.

In this example, programmer 120 is an external computing device that is configured to wirelessly communicate with IMD 114. For example, programmer 120 may be a clinician programmer that the clinician uses to communicate with IMD 114. Alternatively, programmer 120 may be a patient programmer that allows patient 112 to view and modify therapy parameters. The clinician programmer may include more programming features than the patient programmer. In other words, more complex or sensitive tasks may only be allowed by the clinician programmer to prevent patient 112 from making undesired changes to IMD 114.

Programmer 120 may be a hand-held computing device that includes a display viewable by the user and a user input mechanism that can be used to provide input to programmer 120. For example, programmer 120 may include a small display screen (e.g., a liquid crystal display or a light emitting diode display) that presents information to the user. In addition, programmer 120 may include a keypad, buttons, a peripheral pointing device, touch screen or another input mechanism that allows the user to navigate through the user interface of programmer 120 and provide input.

If programmer 120 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 120 may be a touch screen that allows the user to provide input directly to the user interface shown on the display. The user may use a stylus or their finger to provide input to the display.

In other examples, rather than being a handheld computing device or a dedicated computing device, programmer 120 may be a larger workstation or a separate application within another multi-function device. For example, the multi-function device may be a cellular phone or personal digital assistant that can be configured to an application to simulate programmer 120. Alternatively, a notebook computer, tablet computer, or other personal computer may enter an application to become programmer 120 with a wireless adapter connected to the personal computer for communicating with IMD 114.

When programmer 120 is configured for use by the clinician, programmer 120 may be used to transmit initial programming information to IMD 114. This initial information may include system 110 hardware information such as the type of lead 116, the position of lead 116 within patient 112, the therapy parameter values of therapy programs stored within IMD 114 or within programmer 120, and any other information the clinician desires to program into IMD 114.

With the aid of programmer 120 or another computing device, a clinician may select values for therapy parameters for controlling therapy delivery by therapy system 110. The values for the therapy parameters may be organized into a group of parameter values referred to as a "therapy program" or "therapy parameter set." "Therapy program" and "therapy parameter set" are used interchangeably herein. In the case of electrical stimulation, the therapy parameters may include an electrode combination, and an amplitude, which may be a current or voltage amplitude, and, if IMD 114 delivers electrical pulses, a pulse width, and a pulse rate for stimulation signals to be delivered to the patient. An electrode combination may include a selected subset of one or more electrodes 117 located on one or more implantable leads 116 coupled to IMD 114. The electrode combination may also refer to the polarities of the electrodes in the selected subset. By selecting particular electrode combinations, a clinician may target particular anatomic structures within brain 118 of patient 112. In addition, by selecting values for amplitude, pulse width, and pulse rate, the physician can attempt to generate an efficacious therapy for patient 112 that is delivered via the selected electrode subset. Due to physiological diversity, condition differences, and inaccuracies in lead placement, the parameters may greatly vary between patients.

During a programming session, the clinician may determine one or more therapy programs that may provide effective therapy to patient 112. Patient 112 may provide feedback to the clinician as to the efficacy of the specific program being evaluated. Once the clinician has identified one or more programs that may be beneficial to patient 112, patient 112 may continue the evaluation process and determine which program best alleviates the condition of patient 112 or otherwise provides efficacious therapy to patient 112. Programmer 120 may assist the clinician in the creation/identification of therapy programs by providing a methodical system of identifying potentially beneficial therapy parameters.

In some examples, the clinician may select therapy parameters using the techniques described in U.S. Pat. Appl. Pub. Nos. 2007/0203546 (Stone et al.) and 2007/0203541 (Goetz et al.), which describe programming systems and methods that support the programming of stimulation parameters with a therapy system 110 including a lead 116, which may include a complex electrode array geometry.

In accordance with techniques described in U.S. Pat. Appl. Pub. No. 2007/0203546 (Stone et al.), a user interface of programmer 120 may display a representation of the anatomical regions of patient 112, such as anatomical regions of brain 118. The three-dimensional (3D) space of the anatomical regions may be displayed as multiple two-dimensional (2D) views or a 3D visualization environment. Lead 116 may also be represented on the display of the user interface, positioned according to the actual implantation location by the clinician or directly from an image taken of the lead within brain 118. The clinician may interact with the user interface of programmer 120 to manually select and program certain electrodes of lead 116, select an electrode level of the lead and adjust the resulting stimulation field with the anatomical regions as guides, or defining one or more stimulation fields that only affect anatomical regions of interest. Once the clinician has defined the one or more stimulation fields, system 110 automatically generates the stimulation parameter values associated with each of the stimulation fields and transmits the parameter values to IMD 114. The stimulation parameter values may be stored as therapy programs within a memory of IMD 114 and/or a memory within programmer 120.

In accordance with techniques described in U.S. Pat. Appl. Pub. No. 2007/0203541 (Goetz et al.), programmer 120 may present a user interface that displays electrodes of lead 116 and enables a user to select individual electrodes to form an electrode combination and specify parameters for stimulation delivered via the electrode combination. In accordance with other techniques described in U.S. Pat. Appl. Pub. No. 2007/0203541 (Goetz et al.), programmer 120 may present a user interface to a user that enables the user to manipulate a representation of an electrical stimulation field (i.e., one type of therapy field) produced by a selected electrode combination. A processor within programmer 120 may then select the appropriate electrode combination, electrode polarities, amplitudes, pulse widths, and pulse rates of electrical stimulation sufficient to support the field manipulation operations inputted by the user into programmer 120. That is, programmer 120 may automatically generate a therapy program that best fits a stimulation field created by a user via a user interface of programmer 120.

Programmer 120 may also be configured for use by patient 112. When configured as the patient programmer, programmer 120 may have limited functionality in order to prevent patient 112 from altering critical functions or applications that may be harmful to patient 112. In this manner, programmer 120 may only allow patient 112 to adjust certain therapy parameters or set an available range of values for a particular therapy parameter. Programmer 120 may also provide an indication to patient 112 when therapy is being delivered or when the power source within programmer 120 or IMD 114 need to be replaced or recharged.

Whether programmer 120 is configured for clinician or patient use, programmer 120 may communicate with IMD 114 or any other computing device via wireless communication. Programmer 120, for example, may communicate via wireless communication with IMD 114 using radio frequency (RF) telemetry techniques known in the art. Programmer 120 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 120 may also communicate with another programming or computing device via exchange of removable media, such as magnetic or optical disks, or memory cards or sticks. Further, programmer 120 may communicate with IMD 114 and other another programmer via remote telemetry techniques known in the art, communicating via a local area network (LAN), wide area network (WAN), public switched telephone network (PSTN), or cellular telephone network, for example.

In other applications of therapy system 110, the target therapy delivery site within patient 112 may be a location proximate to a spinal cord or sacral nerves (e.g., the S2, S3 or S4 sacral nerves) in patient 112 or any other suitable nerve, organ, muscle or muscle group in patient 112, which may be selected based on, for example, a patient condition. For example, therapy system 110 may be used to deliver an electrical stimulation to tissue proximate to a pudendal nerve, a perineal nerve or other areas of the nervous system, in which cases, lead 116 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain). In addition, although a single lead 116 is shown in FIG. 7A, in some therapy systems, two or more leads may be electrically coupled to IMD 114.

Figure 7B:
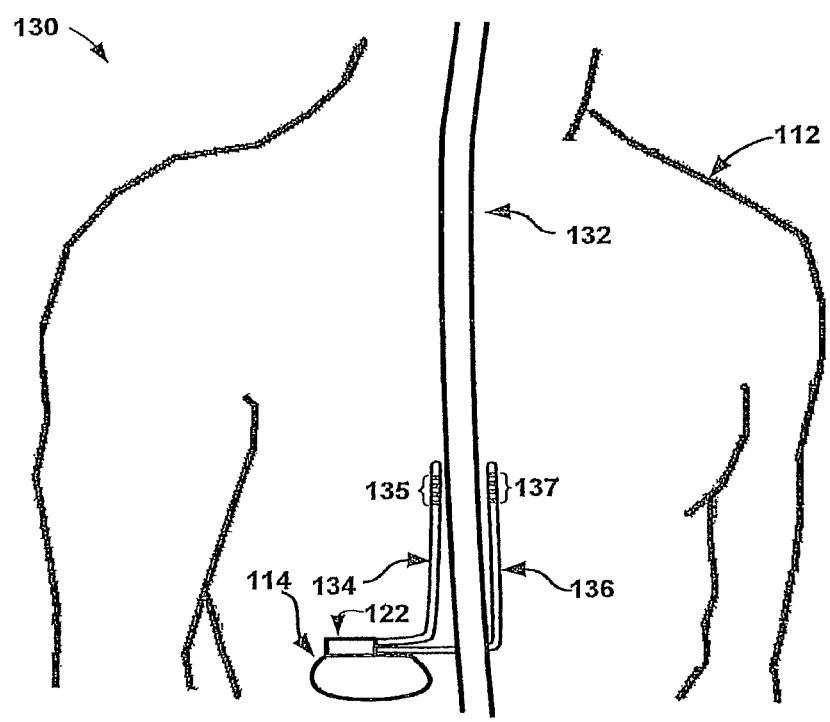
FIG. 7B is a conceptual diagram of another example of an implantable medical device system (e.g., therapy system) that delivers electrical stimulation to target tissue sites proximate to the spine of a patient according to the present disclosure.

FIG. 7B is a conceptual diagram of another example of an implantable medical device system (e.g., therapy system) 130 that delivers electrical stimulation to target tissue sites proximate to spinal cord 132 of patient 112. Therapy system 130 includes IMD 114, which is coupled to leads 134, 136 via connector block 122. Leads 134, 136 each include an array of electrodes 135, 137, respectively. IMD 114 may deliver stimulation to patient 112 via a combination of electrodes 135, 137. Electrodes 135, 137 may each be any suitable type of electrode, such as a ring electrode, partial ring electrode or segmented electrode.

In some examples, the array of electrodes 135, 137 may also include at least one sense electrode that senses a physiological parameter of patient 112, such as, but not limited to, a heart rate, respiration rate, respiratory volume, core temperature, muscular activity, electromyogram (EMG), an electroencephalogram (EEG), an electrocardiogram (ECG) or galvanic skin response. Therapy systems 110, 130 may also include sensor 126 (shown in FIG. 7A, not shown in FIB. 7B) in addition to or instead of sense electrodes on the leads 116, 134, 136. Sensor 126 may be a sensor configured to detect an activity level, posture, or another physiological parameter of patient 112. For example, sensor 126 may generate a signal that changes as a function of the physiological parameter of patient 112. Sensor 126 may be implanted or external to patient 112, and may be wirelessly coupled to IMD 114 or via a lead, such as leads 116, 134, 136, or another lead. For example, sensor 126 may be implanted within patient 112 at a different site than IMD 114 or sensor 126 may be external. In some examples, sensor 126 may be incorporated into a common housing with IMD 114. In addition to, or instead of, being coupled to IMD 114, in some cases, sensor 126 may be wirelessly coupled to programmer 120 or coupled to programmer 120 by a wired connection.

In the example shown in FIG. 7B, leads 134, 136 are positioned to deliver bilateral stimulation to patient 112, i.e., stimulation signals are delivered to target tissue sites on opposite sides of a midline of patient 112. The midline may generally be defined along spinal cord 132. Just as with therapy system 110, a clinician may generate one or more therapy programs for therapy system 130 by selecting values for one or more types of therapy parameters that provide efficacious therapy to patient 112 with the aid of programmer 120 or another computing device. The therapy parameters may include, for example, a combination of the electrodes of leads 134 and/or 136, the voltage or current amplitude, pulse width, and frequency of stimulation.

Figure 8:
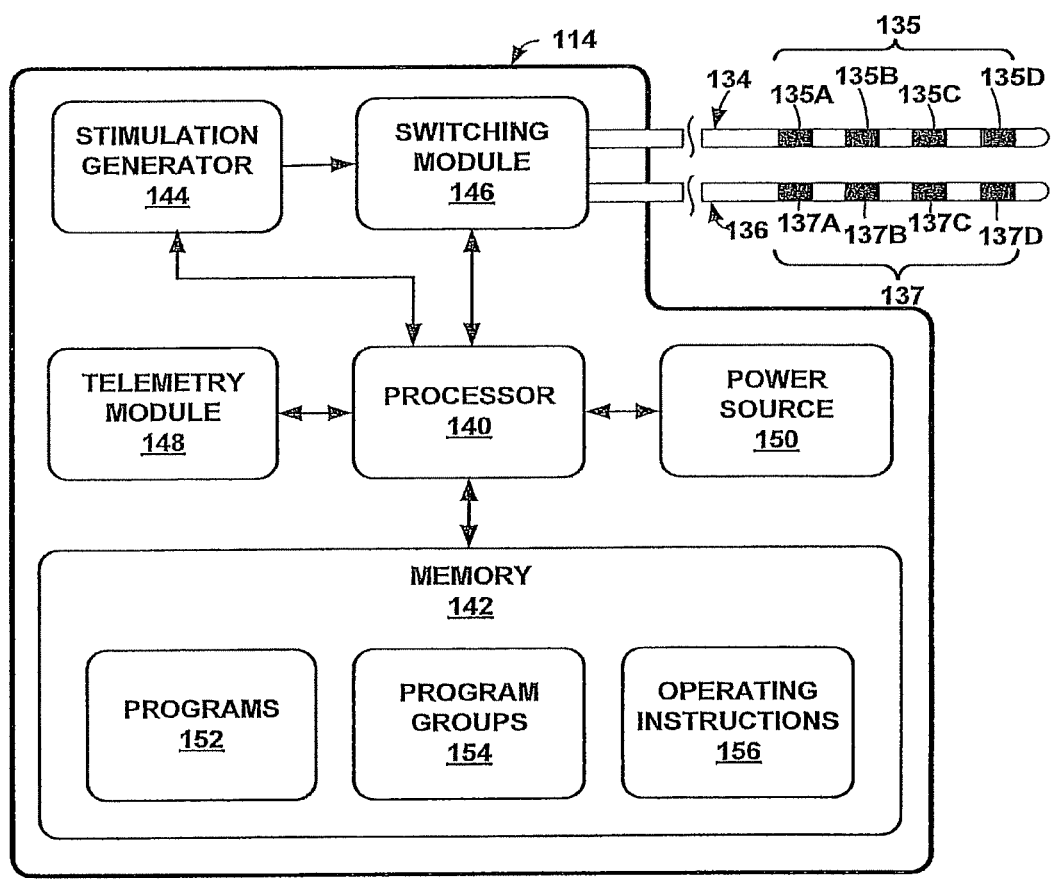
FIG. 8 is a functional block diagram of an exemplary IMD of the present disclosure.

FIG. 8 is a functional block diagram of an exemplary IMD 114. IMD 114 includes a processor 140, memory 142, stimulation generator 144, switching module 146, telemetry module 148, and power source 150. Herein, for IMD 114, the processor 140, memory 142, stimulation generator 144, switching module 146, and telemetry module 148 are collectively referred to as "control electronics." As shown in FIG. 8, stimulation generator 144 is coupled to leads 134, 136, for example, via switching module 146. Alternatively, stimulation generator 144 may be coupled to a single lead (e.g., as shown in FIG. 7A) or more than three leads directly or indirectly (e.g., via a lead extension, such as a bifurcating lead extension that may electrically and mechanically couple to two leads) as needed to provide stimulation therapy to patient 112.

In the example illustrated in FIG. 8, lead 134 includes electrodes 135A-135D (collectively referred to as "electrodes 135") and lead 136 includes electrodes 137A-137D (collectively referred to as "electrodes 137"). Electrodes 135, 137 may be ring electrodes. In other examples, electrodes 135, 137 may be arranged in a complex electrode array that includes multiple non-contiguous electrodes at different angular positions about the outer circumference of the respective lead 134, 136, as well as different levels of electrodes spaced along a longitudinal axis of the respective lead 134, 136. The configuration, type, and number of electrodes 135, 137 illustrated in FIG. 8 are merely exemplary. In other examples, IMD 114 may be coupled to any suitable number of leads with any suitable number and configuration of electrodes.

Memory 142 includes computer-readable instructions that, when executed by processor 140, cause IMD 114 to perform various functions. Memory 142 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 142 may include programs 152, program groups 154, and operating instructions 156 in separate memories within memory 142 or separate areas within memory 142. Each program 152 defines a particular program of therapy in terms of respective values for electrical stimulation parameters, such as electrode combination, electrode polarity, current or voltage amplitude, pulse width and pulse rate. A program group 154 defines a group of programs that may be delivered together on an overlapping or non-overlapping basis. Operating instructions 156 guide general operation of IMD 114 under control of processor 140, and may include instructions for measuring, for example, the impedance of electrodes 135, 137 and/or determining the distance between electrodes 135, 137.

Stimulation generator 144 produces stimulation signals, which may be pulses as primarily described herein, or continuous time signals, such as sine waves, for delivery to patient 112 via selected combinations of electrodes 135, 137. Processor 140 controls stimulation generator 144 according to programs 152 and program groups 154 stored in memory 142 to apply particular stimulation parameter values specified by one or more of programs, such as amplitude, pulse width, and pulse rate. Processor 140 may include a microprocessor, a controller, a digital signal processor (DSP), an application specific integrated circuit (ASIC), a field-programmable gate array (FPGA), or equivalent discrete or integrated digital or analog logic circuitry, and the functions attributed to processor 140 herein may be embodied as software, firmware, hardware or any combination thereof.

Processor 140 also controls switching module 146 to apply the stimulation signals generated by stimulation generator 144 to selected combinations of electrodes 135, 137. In particular, switching module 146 couples stimulation signals to selected conductors within leads 134, 136 which, in turn, deliver the stimulation signals across selected electrodes 135, 137. Switching module 146 may be a switch array, switch matrix, multiplexer, or any other type of switching device suitable to selectively couple stimulation energy to selected electrodes. Hence, stimulation generator 144 is coupled to electrodes 135, 137 via switching module 146 and conductors within leads 134, 136. In some examples, IMD 114 does not include switching module 146.

Stimulation generator 144 may be a single- or multi-channel stimulation generator. In particular, stimulation generator 144 may be capable of delivering, a single stimulation pulse, multiple stimulation pulses, or a continuous signal at a given time via a single electrode combination or multiple stimulation pulses at a given time via multiple electrode combinations. In some examples, however, stimulation generator 144 and switching module 146 may be configured to deliver multiple channels on a time-interleaved basis. In this case, switching module 146 serves to time division multiplex the output of stimulation generator 144 across different electrode combinations at different times to deliver multiple programs or channels of stimulation energy to patient 112.

Telemetry module 148 supports wireless communication between IMD 114 and an external programmer 120 (not shown in FIG. 8) or another computing device under the control of processor 140. Processor 140 of IMD 114 may receive, as updates to programs, values for various stimulation parameters such as amplitude and electrode combination, from programmer 120 via telemetry interface (i.e., module) 148. The updates to the therapy programs may be stored within programs 152 portion of memory 142.

The various components of IMD 114 are coupled to power source 150, which includes a non-rechargeable (i.e., primary) battery as described herein.

Figure 9:
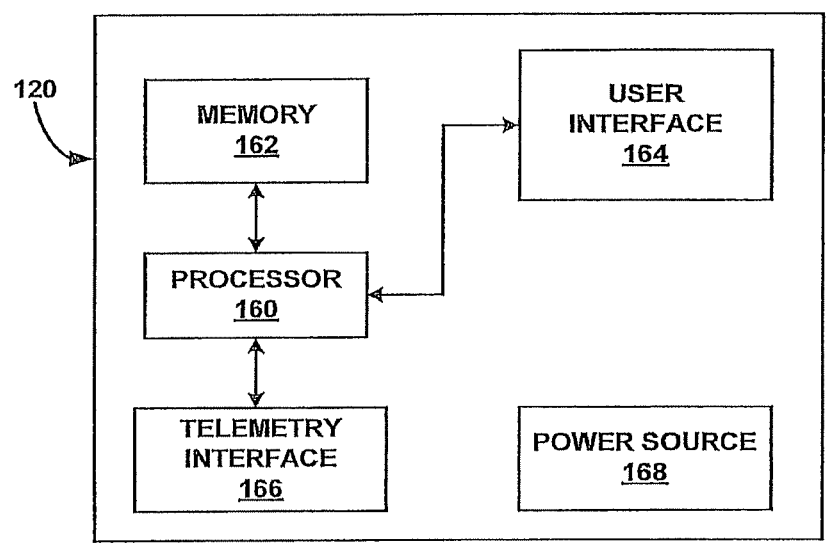
FIG. 9 is a functional block diagram of an exemplary programmer used with an IMD of the present disclosure.

FIG. 9 is a functional block diagram of an example of programmer 120. As shown in FIG. 9, external programmer 120 includes processor 160, memory 162, user interface 164, telemetry module 166 (i.e., telemetry interface), and power source 168. A clinician or another user may interact with programmer 120 to generate and/or select therapy programs for delivery in IMD 114. For example, in some examples, programmer 120 may allow a clinician to define stimulation fields and generate appropriate stimulation parameter values. Processor 160 may store stimulation parameter values as one or more therapy programs in memory 162. Processor 160 may send programs to IMD 114 via telemetry module 166 to control stimulation automatically and/or as directed by the user.

As previously described, programmer 120 may be a handheld computing device, a workstation or another dedicated or multifunction computing device. For example, programmer 120 may be a general purpose computing device (e.g., a personal computer, personal digital assistant (PDA), cell phone, and so forth) or may be a computing device dedicated to, for example, programming IMD 114. Programmer 120 may be one of a clinician programmer or a patient programmer in some examples, i.e., the programmer may be configured for use depending on the intended user. A clinician programmer may include more functionality than the patient programmer. For example, a clinician programmer may include a more featured user interface that allows a clinician to download usage and status information from IMD 114, and allows the clinician to control aspects of IMD 114 not accessible by a patient programmer example of programmer 120.

A user, either a clinician or patient 112, may interact with processor 160 through user interface 164. User interface 164 may include a display, such as a liquid crystal display (LCD), light-emitting diode (LED) display, or other screen, to present information related to stimulation therapy, and buttons or a pad to provide input to programmer 120. In examples where user interface 164 requires a 3D environment, the user interface may support 3D environments such as a holographic display, a stereoscopic display, an autostereoscopic display, a head-mounted 3D display, or any other display that is capable of presenting a 3D image to the user. Buttons may include an on/off switch, plus and minus buttons to zoom in or out or navigate through options, a select button to pick or store an input, and pointing device, e.g. a mouse, trackball, or stylus. Other input devices may be a wheel to scroll through options or a touch pad to move a pointing device on the display. In some examples, the display may be a touch screen that enables the user to select options directly from the display screen.

Processor 160 processes instructions from memory 162 and may store user input received through user interface 164 into memory 162 when appropriate for the current therapy. In addition, processor 160 provides and supports any of the functionality described herein with respect to each example of user interface 164. Processor 160 may comprise any one or more of a microprocessor, DSP, ASIC, FPGA, or other digital logic circuitry, and the functions attributed to processor 160 herein may be embodied as software, firmware, hardware or any combination thereof.

Memory 162 may include instructions for operating user interface 164, telemetry module 166 and managing power source 168. Memory 162 may store program instructions that, when executed by processor 160, cause processor 160 and programmer 120 to provide the functionality ascribed to them herein. Memory 162 also includes instructions for generating therapy programs, such as instructions for determining stimulation parameters for achieving a user-selected stimulation fields or instructions for determining a resulting stimulation field from user-selected stimulation parameters. Memory 162 may include any one or more of a RAM, ROM, EEPROM, flash memory, or the like.

Wireless telemetry in programmer 120 may be accomplished by radio frequency (RF) communication or proximal inductive interaction of programmer 120 with IMD 114. This wireless communication is possible through the use of telemetry module 166. Accordingly, telemetry module 166 may include circuitry known in the art for such communication.

Power source 168 delivers operating power to the components of programmer 120. Power source 168 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary (i.e., non-rechargeable) batteries may be used. In addition, programmer 120 may be directly coupled to an alternating current source, such would be the case with some computing devices, such as personal computers.

The techniques described in this disclosure, including those attributed to IMD 114, programmer 120, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Figure 10:
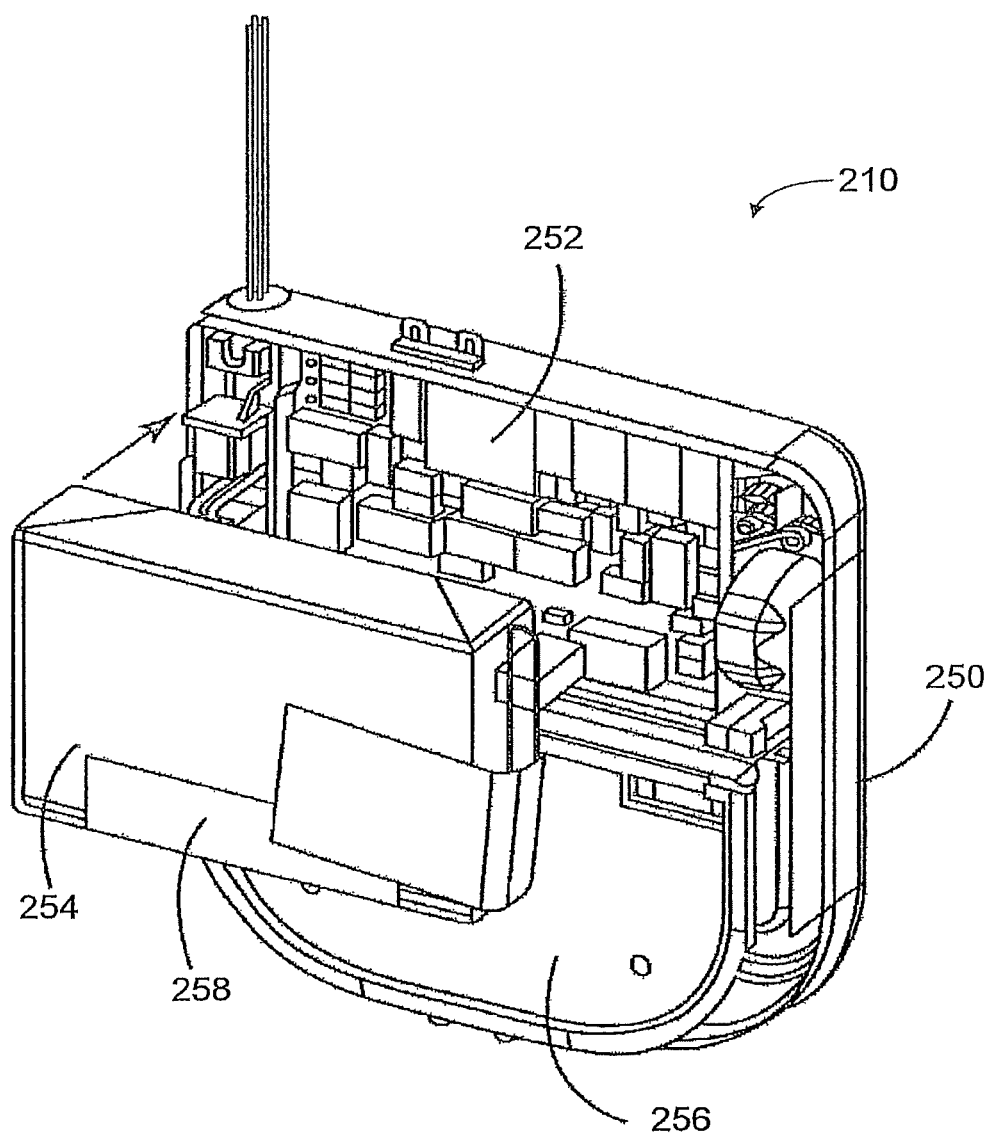
FIG. 10 is a cutaway perspective view of an IMD of the present disclosure.

In a more detailed description, FIG. 10 depicts an IMD 210 that includes a case or housing 250, a control module 252, a battery 254, and one or more capacitor(s) 256. Control module 252 controls one or more sensing and/or stimulation processes from IMD 210 via leads (not shown). Battery 254 includes an insulator 258 disposed therearound. Battery 254 charges capacitor(s) 256 and powers control module 252. For example, in an implantable cardioverter defibrillator, the control module includes components (i.e., control electronics) for delivering therapy and/or monitoring physiological signals, and includes a processor, memory, a stimulation generator that generates at least one of cardiac pacing pulses, defibrillation shocks, and cardioversion shocks, and a sensing module for monitoring a patient's heart rhythm. The capacitors are typically high voltage capacitors (e.g., typically greater than 600 volts for ICDs, although this can vary and is generally known to one of skill in the art what is suitable for various IMD applications). The ICD also includes an implantable medical device battery operably connected to the control electronics to deliver power to the control electronics and operably connected to the capacitors to charge the capacitors.

Figures 11, 12:
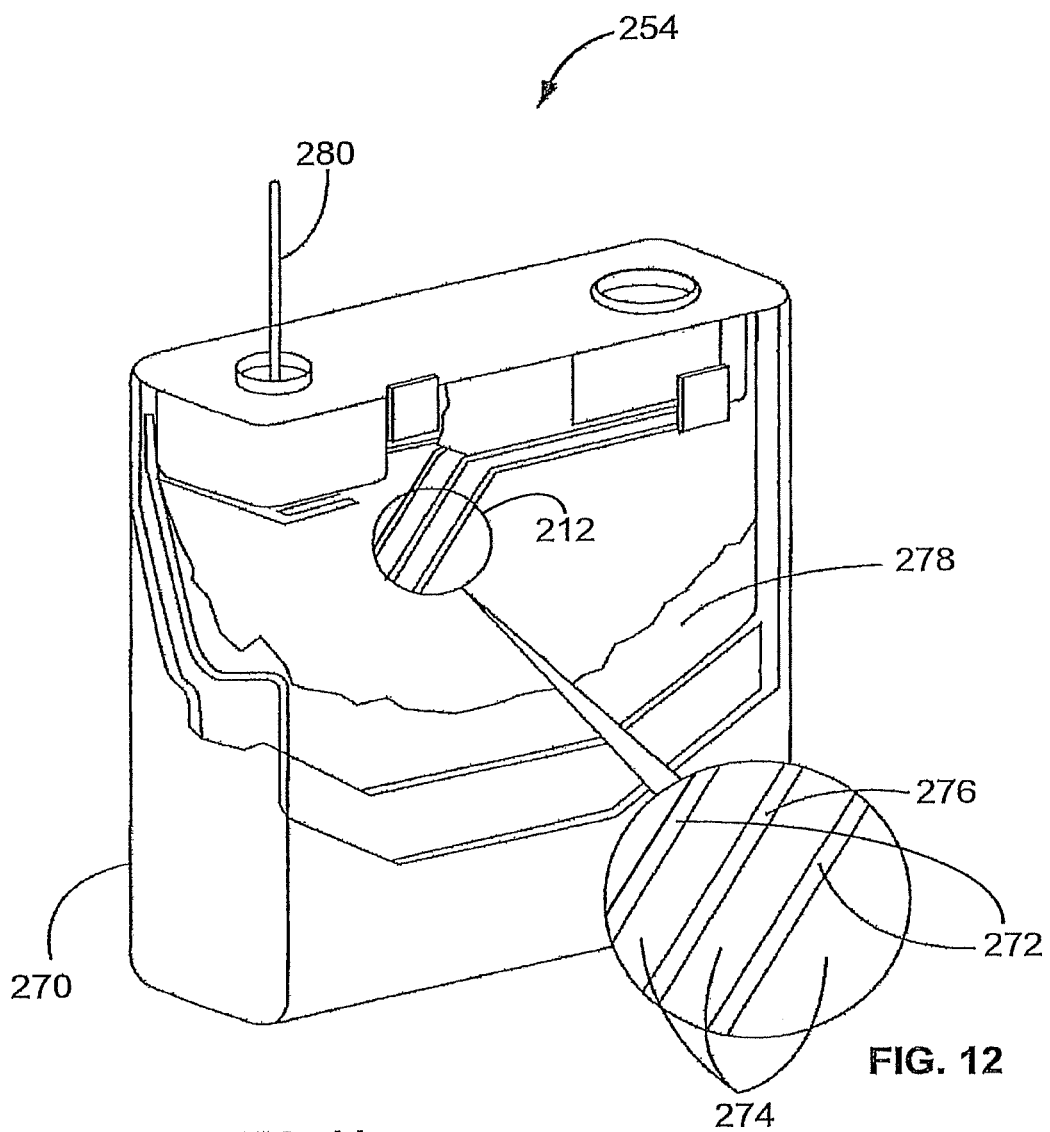
FIG. 11 is a cutaway perspective view of a battery in the IMD of FIG. 10.
FIG. 12 is an enlarged view of a portion of the battery depicted in FIG. 11 and designated by line 212.

FIGS. 11 and 12 depict details of an exemplary battery 254. Battery 254, which as shown includes one cell, includes a case 270, an anode 272, separators 274, a cathode 276, a liquid electrolyte 278, and a feed-through terminal 280. Cathode 276 is wound in a plurality of turns, with anode 272 interposed between the turns of the cathode winding. Separator 274 insulates anode 272 from cathode 276 windings. Case 270 contains the liquid electrolyte 278 to create a conductive path between anode 272 and cathode 276. Electrolyte 278 serves as a medium for migration of ions between anode 272 and cathode 276 during discharge of the cell.

Exemplary ways to construct battery 254 are described, for example, in U.S. Pat. No. 5,439,760 (Howard et al.) and U.S. Pat. No. 6,017,656 (Crespi et al.), and U.S. Pat. Appl. Pub. No. 2006/0166078A1 (Chen et al.).

Exemplary Embodiments of the Disclosure

Embodiment 1 is an implantable medical device comprising a battery cell comprising: an anode; a cathode comprising fluorinated carbon particles; a separator between the anode and the cathode; and an electrolyte contacting the anode, the cathode, and the separator; wherein greater than 50 vol-% of the fluorinated carbon particles have a particle size within a range of 2 microns to 10 microns; and wherein greater than 50% by number of the fluorinated carbon particles have an aspect ratio within a range of 1:1.2 to 1:8.

Embodiment 2 is the device of embodiment 1 wherein greater than 50 vol-% of the fluorinated carbon particles have a particle size within a range of 2 microns to 7 microns, and greater than 50% by number have an aspect ratio within a range of 1:1.2 to 1:4.

Embodiment 3 is the device of embodiment 2 wherein greater than 50% of the fluorinated carbon particles have a particle size within a range of 2 microns to 5 microns, and greater than 50% by number have an aspect ratio within a range of 1:1.3 to 1:2.

Embodiment 4 is the device of any of embodiments 1 to 3 wherein the fluorinated carbon particles have a BET surface area of greater than 300 $m^2/g$ (or greater than 310 $m^2/g$, or greater than 320 $m^2/g$) and up to 400 $m^2/g$.

Embodiment 5 is the device of any of embodiments 1 to 4 wherein the fluorinated carbon particles comprise a fluorine atomic weight percentage of at least 61%, or at least 63%, or at least 65%.

Embodiment 6 is the device of any of embodiments 1 to 5 wherein the fluorinated carbon particles comprise a fluorine atomic weight percentage of up to 80%, or up to 75%, or up to 71%.

Embodiment 7 is the device of any of embodiments 1 to 6 wherein the fluorinated carbon particles exhibit less than 5% by weight of free carbon.

Embodiment 8 is the device of any of embodiments 1 to 7 wherein the fluorinated carbon has the formula $CF_x$, wherein x is 0.01 to 1.9, preferably 0.1 to 1.5, and more preferably 1.1.

Embodiment 9 is the device of any of embodiments 1 to 8 wherein the fluorinated carbon particles comprise less than 1% by weight of $CF_2$ and $CF_3$.

Embodiment 10 is the device of any of embodiments 1 to 9 wherein the fluorinated carbon particles exhibit an XRD pattern comprising: an area ratio of a 110 peak relative to a 001 peak of ≥4.52%; and a position of a 001 peak centered at ≥13.06° $2\theta_{001}$ Cu Kα.

Embodiment 11 is the device of any of embodiments 1 to 10 wherein the fluorinated carbon particles are formed from fluorinated carbon fibers that are formed from a fibrous carbon precursor.

Embodiment 12 is the device of embodiment 11 wherein the fibrous carbon precursor comprises greater than 95% by weight of carbon, or greater than 99% by weight of carbon.

Embodiment 13 is the device of embodiment 11 or 12 wherein the fibrous carbon precursor comprises polyacrylonitrile.

Embodiment 14 is the device of any of embodiments 1 to 13 wherein the cathode further comprises a metal oxide.

Embodiment 15 is the device of embodiment 14 wherein the metal oxide comprises $MnO_2$.

Embodiment 16 is the device of embodiment 15 wherein the metal oxide comprises silver vanadium oxide.

Embodiment 17 is the device of embodiment 16 wherein the fluorinated carbon particles and silver vanadium oxide are present in the cathode in amounts within a range of 0.3:1 to 10:1.

Embodiment 18 is the device of embodiment 17 wherein the fluorinated carbon particles and silver vanadium oxide are present in the cathode in amounts within a range of 1:1 to 10:1.

Embodiment 19 is the device of embodiment 17 wherein the fluorinated carbon particles and silver vanadium oxide are present in the cathode in amounts within a range of 0.3:1 to 3.5:1.

Embodiment 20 is the device of embodiment 18 or 19 wherein the fluorinated carbon particles and silver vanadium oxide are actives present in the cathode in a total amount of 80 wt-% to 96 wt-%, or 85 wt-% to 92 wt-%, or 88 wt-% to 92 wt-%, based on the total weight of the cathode.

Embodiment 21 is the device of any of embodiments 1 to 20 wherein the cathode further comprises a conductivity enhancer.

Embodiment 22 is the device of embodiment 21 wherein the conductivity enhancer comprises a conductive carbon.

Embodiment 23 is the device of any of embodiments 1 to 22 wherein the cathode further comprises a binder.

Embodiment 24 is the device of embodiment 23 wherein the binder comprises polytetrafluoroethylene (PTFE).

Embodiment 25 is an implantable medical device comprising a battery cell comprising: an anode comprising lithium; a cathode comprising milled fluorinated carbon fibers; a separator between the anode and the cathode; and an electrolyte contacting the anode, the cathode, and the separator; wherein greater than 50 vol-% of the milled fluorinated carbon fibers have a particle size within a range of 2 microns to 10 microns; and wherein 50% by number of the milled fluorinated carbon fibers have an aspect ratio within a range of 1:1.2 to 1:8.

Embodiment 26 is a non-rechargeable battery comprising: an anode comprising lithium; a cathode comprising fluorinated carbon particles and a metal oxide; a separator between the anode and the cathode; and an electrolyte contacting the anode, the cathode, and the separator; wherein greater than 50 vol-% of the fluorinated carbon particles have a particle size within a range of 2 microns to 10 microns; and wherein greater than 50% by number have an aspect ratio within a range of 1:1.2 to 1:8.

Embodiment 27 is an implantable medical device comprising: control electronics for delivering therapy and/or monitoring physiological signals, the control electronics comprising: a processor; and memory; and an implantable medical device battery operably connected to the control electronics to deliver power to the control electronics. The battery comprises: an anode comprising lithium; a cathode comprising fluorinated carbon particles; a separator between the anode and the cathode; and an electrolyte contacting the anode, the cathode, and the separator; wherein the cathode comprises a layer on each major surface of the single current collector, wherein the layer comprises a mixture comprising a metal oxide and fluorinated carbon particles; wherein greater than 50 vol-% of the fluorinated carbon particles have a particle size within a range of 2 microns to 10 microns; and wherein greater than 50% by number have an aspect ratio within a range of 1:1.2 to 1:8.

Embodiment 28 is an implantable medical device system comprising: an implantable medical device of embodiment 27; and components operably attached to the implantable medical device for delivering therapy and/or monitoring physiological signals.

Embodiment 29 is a method of making a battery cell for use in an implantable medical device, the method comprising: providing a fibrous carbon precursor; forming fluorinated carbon fibers from the fibrous carbon precursor; milling the fluorinated carbon fibers to form milled fluorinated carbon fibers; wherein greater than 50 vol-% of the milled fluorinated carbon fibers have a particle size within a range of 2 microns to 10 microns; and wherein greater than 50% by number of the milled fluorinated carbon fibers have an aspect ratio within a range of 1:1.2 to 1:8; forming a cathode comprising the milled fluorinated carbon fibers; providing an anode; providing a separator between the anode and the cathode; providing an electrolyte for activating the anode and the cathode; and combining the cathode, anode, and electrolyte to form a battery cell.

Embodiment 30 is the method of embodiment 29 wherein milling the fluorinated carbon fibers to form milled fluorinated carbon fibers comprises ball milling, jet milling, and/or attritor milling the fluorinated carbon fibers.

Embodiment 31 is the method of embodiment 30 wherein ball milling is performed with a ball to fluorinated carbon fiber volumetric loading ratio of 1:3 and with a container (jar) to fluorinated carbon fiber volumetric loading ratio of 3:1.

Embodiment 32 is the method of any of embodiments 29 to 31 wherein milling the fluorinated carbon fibers to form milled fluorinated carbon fibers comprises ball milling the fluorinated carbon fibers for at least 1 hour, or at least 4 hours, or at least 5 hours, or at least 6 hours, or at least 7 hours, or at least 8 hours.

Embodiment 33 is the method of any of embodiments 29 to 32 wherein milling the fluorinated carbon fibers to form milled fluorinated carbon fibers comprises ball milling the fluorinated carbon fibers for up to 16 hours.

Embodiment 34 is the method of any of embodiments 29 to 33 wherein milling the fluorinated carbon fibers to form milled fluorinated carbon fibers comprises ball milling the fluorinated carbon fibers at a frequency of 100 rpm to 400 rpm.

Embodiment 35 is the method of any of embodiments 29 to 34 wherein the fibrous carbon precursor comprises polyacrylonitrile.

Embodiment 36 is the method of any of embodiments 29 to 35 wherein the milled fluorinated carbon fibers have a BET surface area of greater than 300 $m^2/g$ and up to 400 $m^2/g$.

Embodiment 37 is the method of any of embodiments 29 to 36 wherein greater than 50 vol-% of the milled fluorinated carbon fibers have a particle size within a range of 2 microns to 7 microns, and greater than 50% by number have an aspect ratio within a range of 1:1.2 to 1:4.

Embodiment 38 is the method of embodiment 37 wherein greater than 50 vol-% of the milled fluorinated carbon fibers have a particle size within a range of 2 microns to 5 microns, and greater than 50% by number have an aspect ratio within a range of 1:1.3 to 1:2.

Embodiment 39 is the method of any of embodiments 29 to 38 wherein the milled fluorinated carbon fibers comprise a fluorine atomic weight percentage of at least 61%, or at least 63%, or at least 65%.

Embodiment 40 is the method of any of embodiments 29 to 39 wherein the milled fluorinated carbon fibers comprise a fluorine atomic weight percentage of up to 80%, or up to 75%, or up to 71%.

Embodiment 41 is the method of any of embodiments 29 to 40 wherein the fibrous carbon precursor comprises greater than 95% by weight of carbon, or greater than 99% by weight of carbon.

Embodiment 42 is the method of any of embodiments 29 to 41 wherein the milled fluorinated carbon fibers exhibit less than 5% by weight of free carbon.

Embodiment 43 is the method of any of embodiments 29 to 42 wherein the fluorinated carbon has the formula $CF_x$, wherein x is 0.01 to 1.9, preferably 0.1 to 1.5, and more preferably 1.1.

Embodiment 44 is the method of any of embodiments 29 to 43 wherein the milled fluorinated carbon fibers comprise less than 1% by weight of $CF_2$ and $CF_3$.

Embodiment 45 is the method of any of embodiments 29 to 44 wherein the milled fluorinated carbon fibers exhibit an XRD pattern comprising: an area ratio of a 110 peak relative to a 001 peak of ≥4.52%; and a position of a 001 peak centered at ≥13.06° $2\theta_{001}$ Cu Kα.

Embodiment 46 is the method of any of embodiments 29 to 45 wherein the cathode further comprises a metal oxide.

Embodiment 47 is the method of embodiment 46 wherein the metal oxide comprises $MnO_2$.

Embodiment 48 is the method of embodiment 46 wherein the metal oxide comprises silver vanadium oxide.

Embodiment 49 is the method of embodiment 48 wherein the milled fluorinated carbon fibers and silver vanadium oxide are present in the cathode in amounts within a range of 0.3:1 to 10:1.

Embodiment 50 is the method of embodiment 49 wherein the milled fluorinated carbon fibers and silver vanadium oxide are present in the cathode in amounts within a range of 0.3:1 to 3.5:1.

Embodiment 51 is the method of embodiment 49 or 50 wherein the milled fluorinated carbon fibers and silver vanadium oxide are actives present in the cathode in a total amount of 80 wt-% to 96 wt-%, or 85 wt-% to 92 wt-%, or 88 wt-% to 92 wt-%.

Embodiment 52 is the method of any of embodiments 29 to 51 wherein the cathode further comprises a conductivity enhancer.

Embodiment 53 is the method of embodiment 52 wherein the conductivity enhancer comprises a conductive carbon.

Embodiment 54 is the method of any of embodiments 29 to 53 wherein the cathode further comprises a binder.

Embodiment 55 is the method of embodiment 54 wherein the binder comprises polytetrafluoroethylene (PTFE).

EXAMPLES

Objects and advantages of this disclosure are further illustrated by the following examples, but the particular materials and amounts thereof recited in these examples, as well as other conditions and details, should not be construed to unduly limit this disclosure.

Material Source and/or Specifications

SVO=Silver vanadium oxide in the form of $Ag_2V_4O_{11}$, manufactured by the addition reaction of silver vanadate ($AgVO_3$) and vanadium pentoxide ($V_2O_5$) in a 2:1 mole ratio in an oxygen atmosphere at a temperature of about 520° C., according to the procedure of U.S. Pat. No. 5,221,453 (Crespi).

$CF_x$=Fibrous carbon monofluoride (62-67 wt-% total fluorine, less than 0.10 wt-% free fluorine, X-ray diffraction peak ratio I (2 theta, 25.86)/I (2 theta, 28.64) of less than 1).

Conductive Carbon=Super P carbon, obtained from Imerys Co., Switzerland.

Binder=PTFE, obtained from Daikin Industries, Japan.

Separator=CELGARD 2500, obtained from Celgard, LLC, Charlotte, N.C.

Example 1: Preparation of Milled, Fluorinated Carbon Fibers

Milling of fluorinated carbon fibers ($CF_x$) was performed using a ball roller from Norton (Akron, Ohio). About 50 grams (g) of raw fibrous $CF_x$ was loaded into an Alumina Jar (300-mL capacity). Alumina cylindrical media was added (five 0.5 inch×0.5 inch (1.27 cm×1.27 cm)+five 13/16 inch× 13/16 inch (2.06 cm×2.06 cm)). The jar was placed on the roller assembly, and turned at about 150 revolutions per minute (rpm) for 1 hour, 2 hours, 4 hours, 6 hours, 8 hours, or 16 hours.

Example 2: Analysis of Fluorinated Carbon Particle Size, Aspect Ratio, and Surface Area Particle size distribution (PSD) of the $CF_x$ was determined using a HORIBA (Japan) Laser Scattering Particle Size Distribution Analyzer LA-950. The refractive index used was 1.53. About 200 milligrams (mg) of a $CF_x$ sample was pre-dispersed in about 15 mL isopropyl alcohol and sonicated for a few minutes before analysis. Five thousand (5000) measurement counts were used for the sample and the blank. Table 1 presents the results of the particle size distribution measurements.

TABLE 1

Particle Size Distribution

| Milling Time | D50 |
|---|---|
| Unmilled | 20.1 microns |
| 1 hour | 6.1 microns |
| 2 hours | 5.2 microns |
| 4 hours | 4.2 microns |
| 6 hours | 3.8 microns |
| 8 hours | 3.7 microns |

Figure 13:
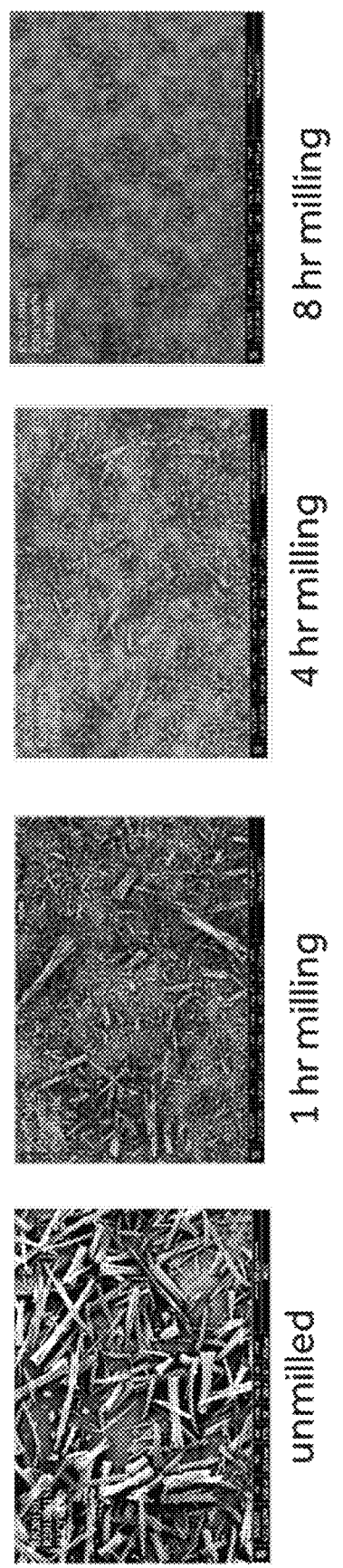
FIG. 13 are Scanning Electron Microscopy micrographs of typical samples of unmilled fluorinated carbon fibers, and fluorinated carbon fibers milled for 1 hour, 4 hours, or 8 hours.

The aspect ratio was obtained from the dimension measurement based on Scanning Electron Microscopy (SEM) micrographs, and was calculated by dividing the long dimension over the short dimension. FIG. 13 shows SEM micrographs of typical samples of unmilled fluorinated carbon fibers, and fluorinated carbon particles formed by milling fluorinated carbon fibers for 1 hour, 4 hours, or 8 hours. Table 2 presents the results of the aspect ratio measurements.

TABLE 2

Aspect Ratios

| Milling Time | Length/Width |
|---|---|
| Unmilled | 10 |
| 1 hour | 7 |
| 4 hours | 4 |
| 6 hours | 2 |
| 8 hours | 1.6 |

The surface area of the fluorinated carbon particles was measured by the Brunauer-Emmett-Teller (BET) method. Table 3 presents the results of the BET measurements.

TABLE 3

Surface Areas Measured by BET Method

| Milling Time | Lot 1 | Lot 2 |
|---|---|---|
| Unmilled | 307.3 cm$^2$/g | 306.9 cm$^2$/g |
| 4 hours | 319.1 cm$^2$/g | 321.7 cm$^2$/g |
| 8 hours | 327.5 cm$^2$/g | 327.5 cm$^2$/g |
| 16 hours | 341.3 cm$^2$/g | 344.2 cm$^2$/g |

Example 3: CF$_x$/SVO Cathode Mix Preparation

The dry cathode mix materials (CF$_x$, SVO, and conductive carbon) were weighed (as an example, for a cathode mix of 100 grams (g), 42 wt-% was CF$_x$, 42 wt-% was SVO, 6 wt-% was carbon, 10 wt-% was PTFE) and added to a mixing container. The mixture was well mixed using a spatula. A mixture of deionized (DI) H$_2$O and isopropyl alcohol (IPA) was added. The wet mixture was then mixed with a spatula until the mixture appeared well mixed. For a 100-g mix batch, about 120 mL of a mixture of water/IPA in a 2:1 ratio was used. The binder (PTFE) emulsion in water/PTFE (about 60 wt-%) was then added to the above mixture, and the mixture was stirred well with a spatula. The mixture was then dried in an oven at 150° C. for about 4 hours. The dried cathode mix was pulverized using a Quadro Pulverizer (Waterloo, Canada).

Example 4: Cathode Pellet Density Measurement and Cohesion Strength

A cathode pellet was pressed by loading 1 g of pulverized cathode mix into a 0.625-inch (1.58 cm) diameter cylindrical die and pressing with a force of 16 tons (16000 kg).

The diameter and thickness of the pressed pellet were measured with a drop gauge. Cathode geometric density was calculated by dividing the mass by the pellet volume.

Figure 14:
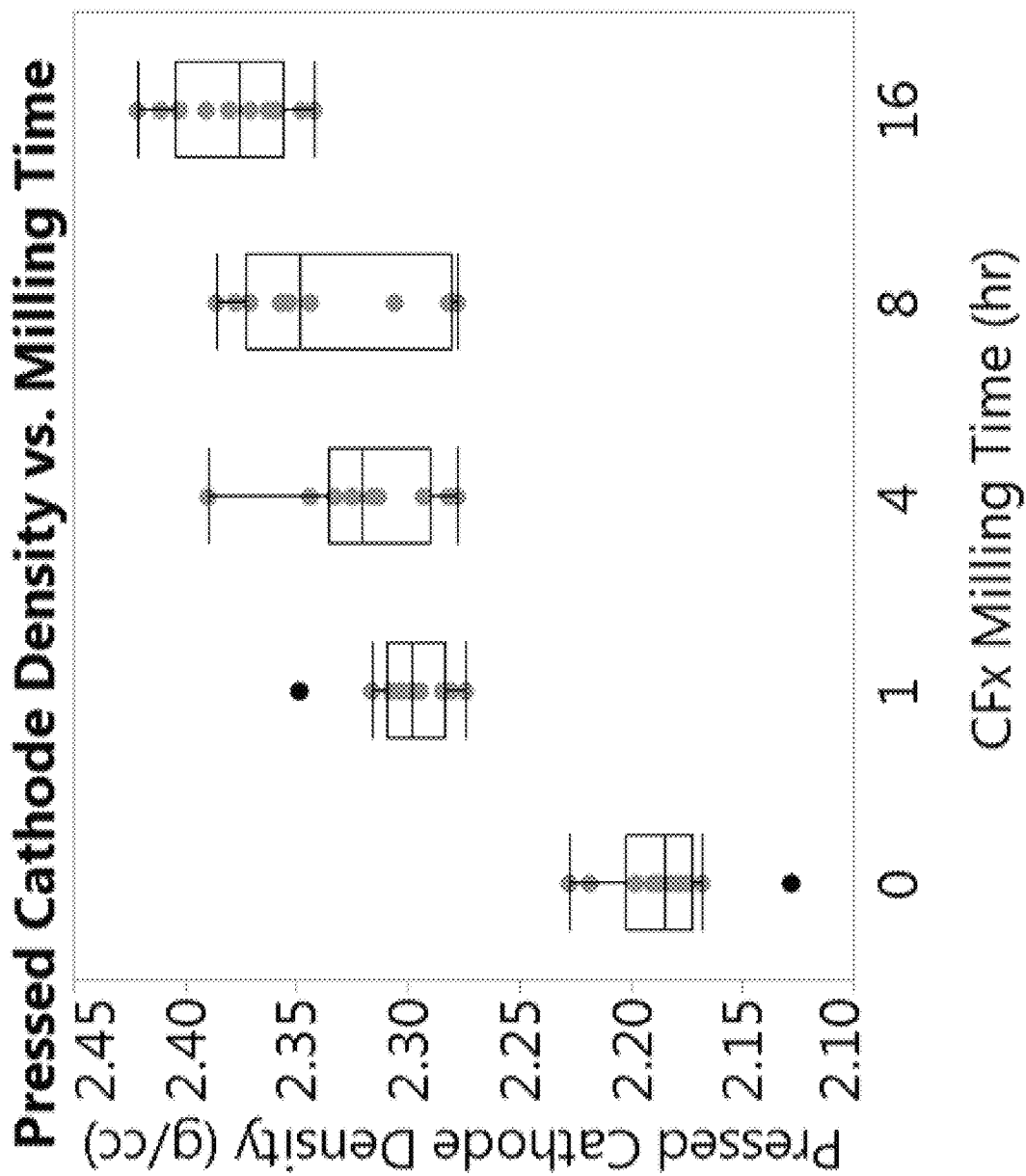
FIG. 14 is a graph of cathode pellet density vs milling time of $CF_x$.

FIG. 14 shows the effect of CF$_x$ milling on the density of the pressed cathode pellets. The cathode mixes were prepared with a CF$_x$ to SVO weight ratio of 1:1 and an active (CF$_x$ and SVO) weight percentage of 90%. As shown in FIG. 14, mixes with milled CF$_x$ (milling times 1, 4, 8, and 16 hours) have a significantly higher density than mixes with unmilled CF$_x$ (milling time 0).

Figure 15:
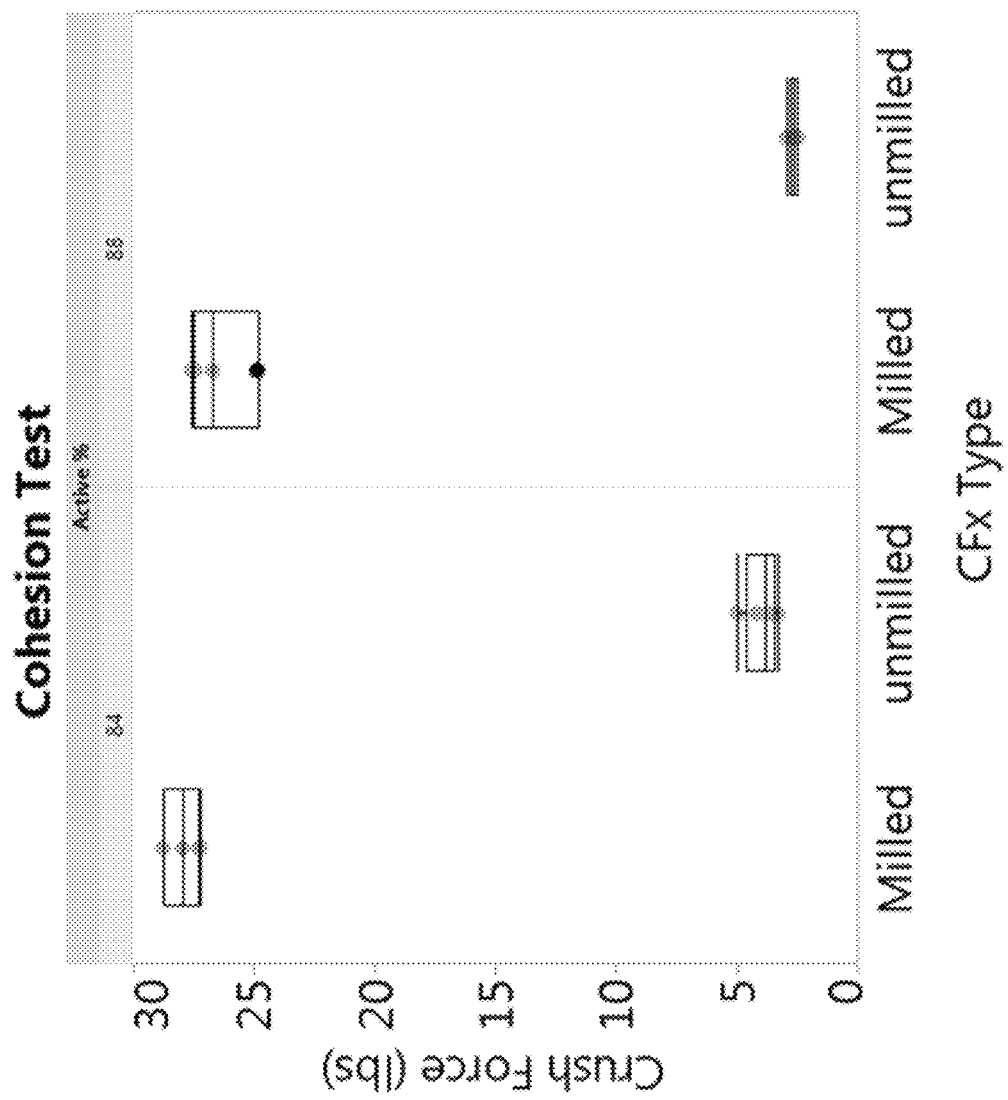
FIG. 15 is a chart of crush force determined by the Cohesion Test of pressed cathode pellets.

The cohesion strength of the pressed cathode pellets was evaluated by measuring the yield load (crush force) when subjected to a force perpendicular to the pellet plane. The load was applied and measured with an MTS 858 Mini Bionix II (Eden Prairie, Minn.). FIG. 15 shows the crush force of pressed pellets (1 g) constructed using cathode mixes containing unmilled and milled CF$_x$. Results of mixes with two compositions are shown: one with 88% active cathode materials; the other with 84% active cathode materials. Mixes shown in FIG. 15 have the same CF$_x$ to SVO ratio as those in FIG. 14. Cathode pellets with milled CF$_x$ exhibited a significant increase in cohesion strength as measured by a larger yield force, compared to unmilled material.

Example 5: Preparation of Cell Assembly and Discharge

Coin cells were prepared using lithium metal anodes, two layers of microporous separator, and pulverized cathode mix. The cathode was formed by pressing a quantity of pulverized cathode mix onto titanium mesh current collectors. The cells were filled with an electrolyte mixture comprising 1.0 M LiAsF$_6$ in a 50:50 volume mixture of propylene carbonate (PC) and dimethoxyethane (DME).

Cells were discharged at 37° C. at C/100 to C/1000 rate.

Example 6: Determination of Volumetric Capacity and Specific Capacity

Volumetric capacity (mAh/cc) is calculated by multiplying the measured geometric density (g/cc) of the cathode pellet by the useful specific capacity of CF$_x$ (mAh/g). The useful specific capacity of CF$_x$ is 91% of the theoretical specific capacity of CF$_x$, which is 1 electron per CF$_{1.0}$.

The volumetric capacity results are shown in Table 4. The mixes of Table 4 had the same compositions as those in FIG. 14 (cathode geometric density). These results indicate that the higher geometric densities of the pellets lead to higher volumetric capacities.

TABLE 4

Volumetric Capacity Comparison

| Milling Time | Cathode Volumetric Capacity, mAh/cc | Percent Increase (Relative to Unmilled) |
|---|---|---|
| Unmilled | 1046 | NA |
| 1 hour | 1104 | 5.5% |
| 4 hours | 1114 | 6.5% |
| 8 hours | 1123 | 7.4% |
| 16 hours | 1138 | 8.8% |

Table 5 compares the specific capacity of cathodes with unmilled fluorinated carbon fibers and with milled fluorinated carbon fibers for 4 hours, 8 hours, and 16 hours (normalized to the specific capacity of the unmilled fluorinated carbon fibers).

Figure 16:
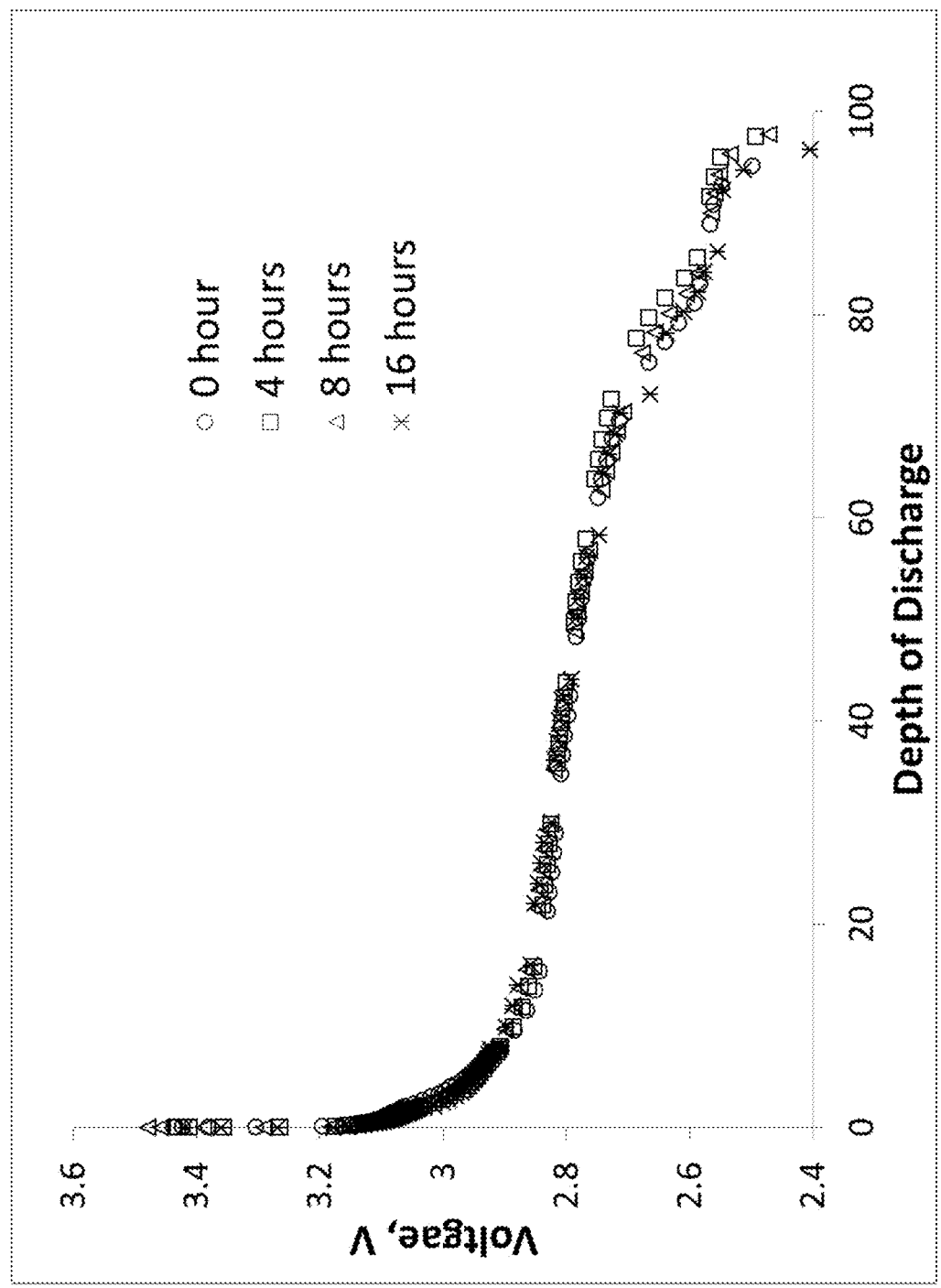
FIG. 16 shows the discharge results of cathodes from fluorinated carbon fibers and milled fluorinated carbon fibers.
Figure 17:
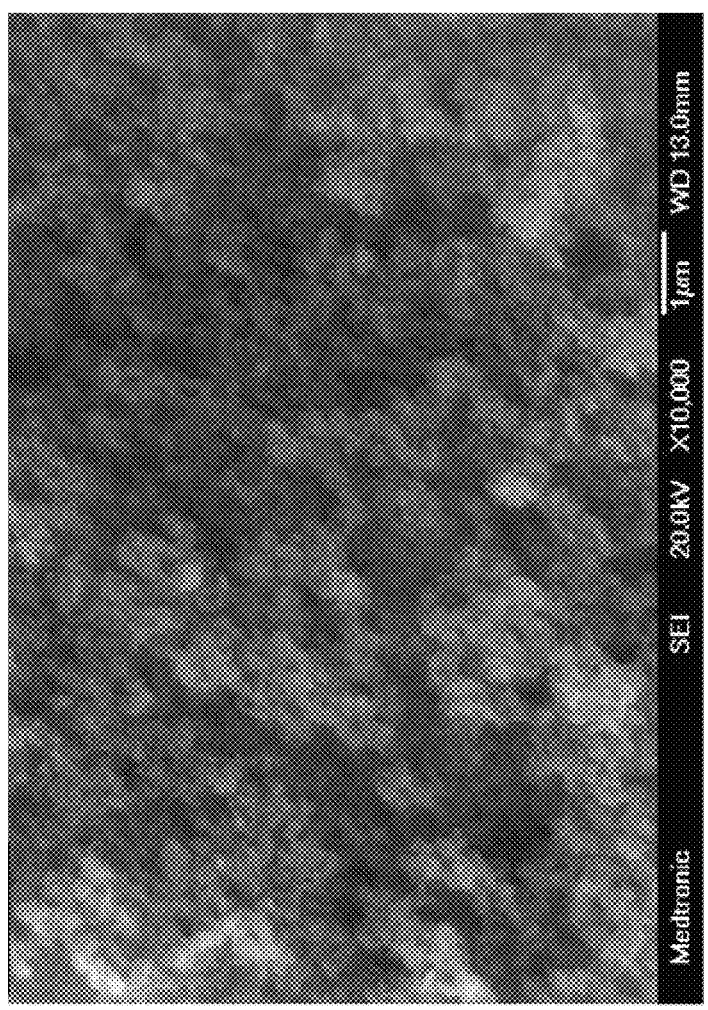
FIG. 17 is a Scanning Electron Microscopy micrograph of fluorinated micron-sized carbon spheres.

FIG. 16 demonstrates that the cathodes containing milled $CF_x$ deliver the same (deliverable) capacity as cathodes produced with the same cathode composition, but containing unmilled $CF_x$.

In no cases did the milling reduce the specific capacity. Mixes in Table 5 had the same compositions as those in FIG. 14 (cathode geometric density).

TABLE 5

Specific Capacity Comparison

| Milling Time | Cathode Specific Capacity, mAh/g |
|---|---|
| Unmilled | 480 |
| 4 hours | 483 |
| 8 hours | 480 |
| 16 hours | 481 |

In practice, milled fluorinated carbon fibers not only retained the high specific capacity of the unmilled fluorinated carbon fibers (Table 5), but also supported increased geometric density of the cathode (FIG. 14), increasing the volumetric capacity of the cathode (Table 4).

Example 7: $CF_x$ Cathode Mix Preparation $CF_x$ cathode mixes were produced using each of the previously described unmilled $CF_x$ fibers, milled $CF_x$ fibers, and commercially obtained sub-micron sized $CF_x$ spheres. The latter were produced by fluorination of sub-micron sized carbon spheres. The mixes were produced using the process described in Example 3, with the exception that the cathodes comprise 80 wt-% $CF_x$, 5 wt-% carbon, and 15 wt-% PTFE.

U.S. Pat. No. 9,466,838 (Reddy et al.) teaches that the performance of $CF_x$ cells can be improved under high current discharge by milling the material and achieving high surface area (250-300 $m^2/g$).

Table 6 compares the Volumetric Capacity of the cathodes described in Example 7. While each of the $CF_x$ materials has high surface area (approximately 310-340 $m^2/g$), the data demonstrate the surprising result that surface area alone does not predict performance. It was discovered that an optimal aspect ratio is also needed to maximize capacity density. It is possible that particles of certain aspect ratios (1:1.2-1:8) and high surface area may pack most efficiently in the cathode, leading to high capacity density. Thus, reduced particle size is not sufficient to provide improved performance.

TABLE 6

Comparison of Volumetric Capacity of Cathodes Made with Various $CF_x$ Powders

| Material | Surface Area | Milled? | Particle Aspect Ratio | Volumetric Capacity |
|---|---|---|---|---|
| Sub-Micron Spheres | 330 $m^2/g$ | No | 1:1 | 1052 mAh/cc |
| Sub-Micron Fibers | 307 $m^2/g$ | No | >1:10 | 1046 mAh/cc |
| Milled, Sub-Micron Fibers | 319-344 $m^2/g$ | Yes | 1:1.2-1:8 | 1104-1190 mAh/cc |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

The invention claimed is:

1. An implantable medical device comprising a battery cell comprising:
   an anode;
   a cathode comprising fluorinated carbon particles;
   a separator between the anode and the cathode; and
   an electrolyte contacting the anode, the cathode, and the separator;
   wherein greater than 50 vol-% of the fluorinated carbon particles have a particle size within a range of 2 microns to 10 microns;
   wherein greater than 50% by number of the fluorinated carbon particles have an aspect ratio within a range of 1:1.2 to 1:8; and
   wherein the battery cell has a volumetric capacity of at least 1104 mAh/cc when discharged at 37° C. at C/100 to C/1000 rate.

2. The device of claim 1 wherein greater than 50 vol-% of the fluorinated carbon particles have a particle size within a range of 2 microns to 7 micron, and greater than 50% by number have an aspect ratio within a range of 1:1.2 to 1:4.

3. The device of claim 1 wherein the fluorinated carbon particles have a BET surface area of greater than 300 $m^2/g$ and up to 400 $m^2/g$.

4. The device of claim 1 wherein the fluorinated carbon particles are formed from fluorinated carbon fibers that are formed from a fibrous carbon precursor.

5. The device of claim 1 wherein the cathode further comprises a metal oxide.

6. The device of claim 5 wherein the metal oxide comprises $MnO_2$ or silver vanadium oxide.

7. The device of claim 1 wherein the cathode further comprises a conductivity enhancer comprising a conductive carbon.

8. A non-rechargeable battery comprising:
   an anode comprising lithium;
   a cathode comprising fluorinated carbon particles and a metal oxide;
   a separator between the anode and the cathode; and
   an electrolyte contacting the anode, the cathode, and the separator;
   wherein greater than 50 vol-% of the fluorinated carbon particles have a particle size within a range of 2 microns to 10 microns;
   wherein greater than 50% by number of the fluorinated carbon particles have an aspect ratio within a range of 1:1.2 to 1:8; and
   wherein the battery has a volumetric capacity of at least 1104 mAh/cc when discharged at 37° C. at C/100 to C/1000 rate.

9. An implantable medical device comprising:
   control electronics for delivering therapy and/or monitoring physiological signals, the control electronics comprising:
   a processor; and
   memory; and an implantable medical device battery operably connected to the control electronics to deliver power to the control electronics; the battery comprising:
an anode comprising lithium;
a cathode comprising fluorinated carbon particles;
a separator between the anode and the cathode; and
an electrolyte contacting the anode, the cathode, and the separator;
wherein the cathode comprises a layer on each major surface of the single current collector, wherein the layer comprises a mixture comprising a metal oxide and fluorinated carbon particles;
wherein greater than 50 vol-% of the fluorinated carbon particles have a particle size within a range of 2 microns to 10 microns;
wherein greater than 50% by number of the fluorinated carbon particles have an aspect ratio within a range of 1:1.2 to 1:8; and
wherein the battery has a volumetric capacity of at least 1104 mAh/cc when discharged at 37° C. at C/100 to C/1000 rate.

10. An implantable medical device system comprising:
an implantable medical device of claim 1 or 9; and
components operably attached to the implantable medical device for delivering therapy and/or monitoring physiological signals.

* * * * *